(12) United States Patent
Iwahashi et al.

(10) Patent No.: US 6,520,959 B1
(45) Date of Patent: *Feb. 18, 2003

(54) LASER IRRADIATION DEVICE AND METHOD FOR THERAPY OF PROSTATE GLAND BY USE THEREOF

(75) Inventors: Shigenobu Iwahashi, Nakai-machi (JP); Shigeki Ariura, Nakai-machi (JP); Shin Maki, Nakai-machi (JP)

(73) Assignee: Terumo Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/282,458

(22) Filed: Mar. 31, 1999

(30) Foreign Application Priority Data

Mar. 31, 1998 (JP) ............................................ 10-103908
Mar. 31, 1998 (JP) ............................................ 10-103909

(51) Int. Cl.$^7$ ............................................... A61B 18/18
(52) U.S. Cl. ............................... 606/17; 606/18; 606/13
(58) Field of Search ......................... 607/88, 89; 606/2, 606/3, 13, 14, 15, 16, 17, 18

(56) References Cited

U.S. PATENT DOCUMENTS

| | | | |
|---|---|---|---|
| 3,817,635 A | | 6/1974 | Kawahara |
| 4,648,892 A | * | 3/1987 | Kittrell et al. ................. 65/387 |
| 5,128,509 A | * | 7/1992 | Black et al. ........... 219/121.76 |
| 5,143,076 A | * | 9/1992 | Hardy et al. ................. 606/130 |
| 5,292,320 A | | 3/1994 | Brown et al. |
| 5,496,308 A | | 3/1996 | Brown et al. |
| 5,606,981 A | * | 3/1997 | Tartacower et al. ......... 128/772 |
| 5,623,940 A | * | 4/1997 | Daikuzono .................. 128/736 |
| 5,836,941 A | | 11/1998 | Yoshihara et al. |
| 6,379,347 B1 | * | 4/2002 | Maki et al. .................... 606/17 |

FOREIGN PATENT DOCUMENTS

| | | |
|---|---|---|
| EP | 821916 | 2/1998 |
| FR | 2681522 | 3/1993 |
| JP | 2599094 | 6/1994 |
| JP | 7-1711692 | 7/1995 |
| JP | 8-215209 | 8/1996 |
| WO | 93/03678 | 3/1993 |

* cited by examiner

Primary Examiner—Rosiland S. Kearney
(74) Attorney, Agent, or Firm—Burns, Doane, Swecker & Mathis, LLP

(57) ABSTRACT

This invention concerns a lateral-irradiation type laser irradiation device which is capable of effectively irradiating a target site, particularly at a considerable deth, with a laser beam while infallibly and easily preventing normal tissue from injury/and a method for curing prostate gland by the use of the laser irradiation device.

The laser irradiating device 1 moves either or both of the laser probes 3, 4 having the reflecting mirrors 32, 42 provided at the distal end parts of the optical fibers 31, 41 in the longitudinal direction of the sheath 2 so as to alter the interval between the reflecting mirrors 32, 42 and move the position at which the reflected laser beams are concentrated (condensed), namely the target position 5 moves, in the direction perpendicular to the longitudinal axis of the sheath 2.

The method for the therapy of the prostate gland which comprises inserting the laser probes 3, 4 through the urogenital canal, suitably moving the target position 5 at which the laser beams are concentrated, irradiating the ailing site with the laser beams, and curing the ailing site by degeneration or necrosis.

22 Claims, 25 Drawing Sheets

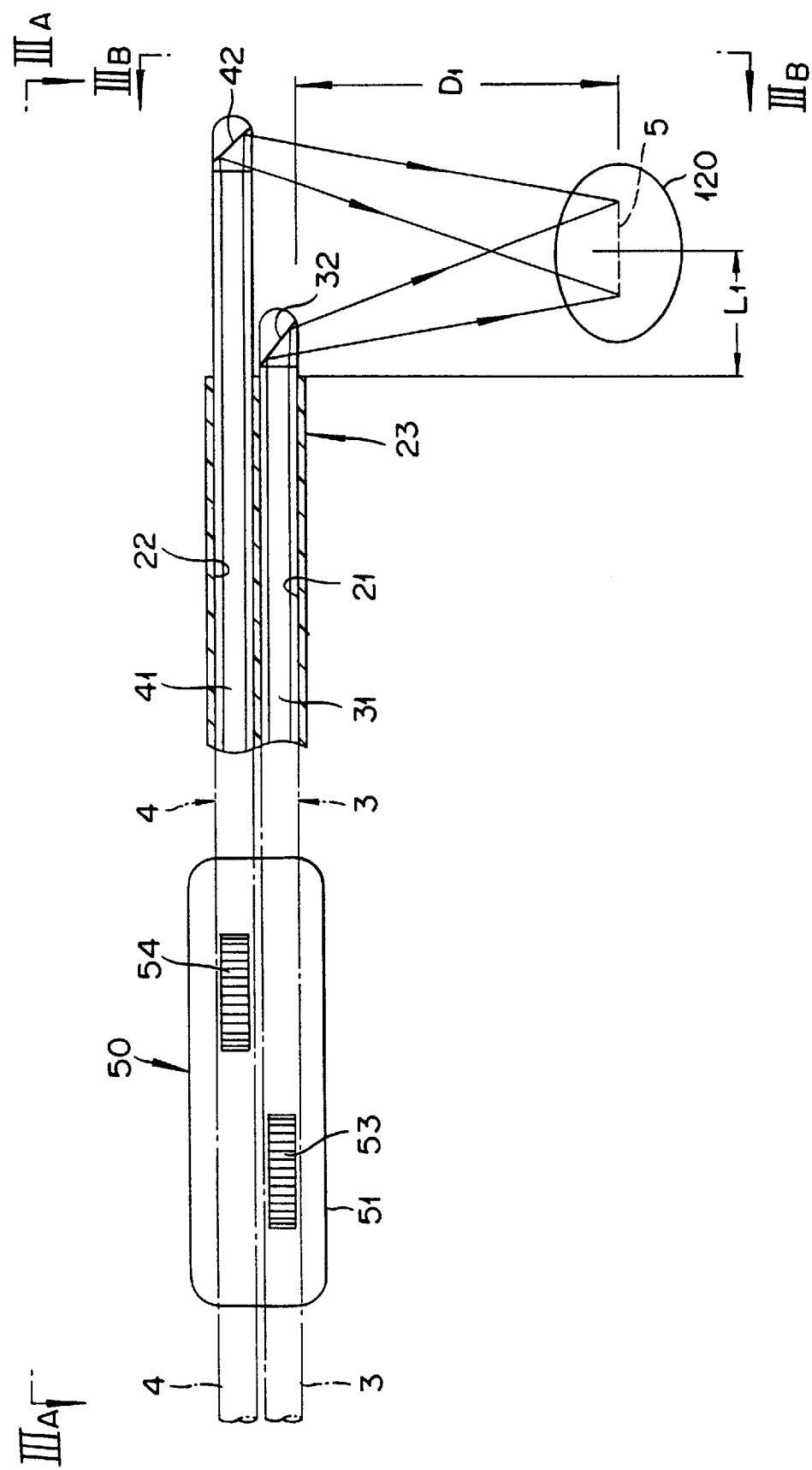

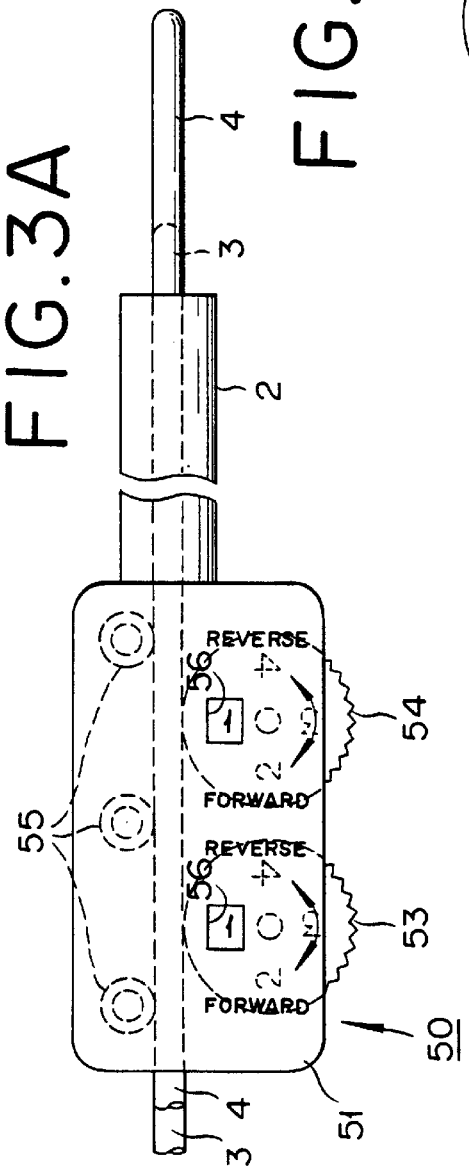
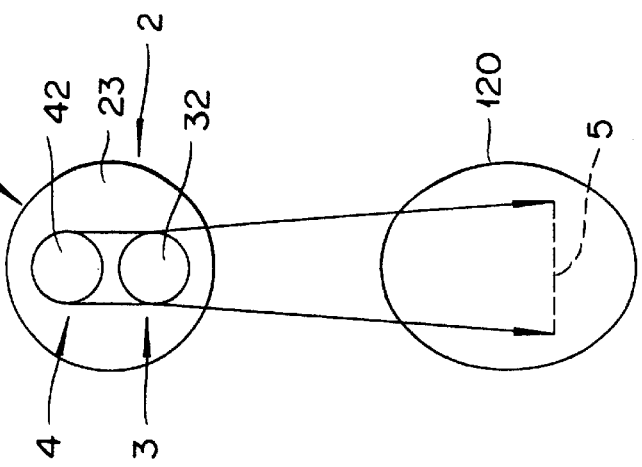
FIG. 3A
FIG. 3B
FIG. 3C
RELATION BETWEEN DIAL NUMBER AND DEPTH $D_1$ (mm) OF IRRADIATION
| DIAL NUMBER FRONT SIDE \ REAR SIDE DIAL NUMBER | 1 | 2 | 3 | 4 |
|---|---|---|---|---|
| 1 | 5 | — | — | — |
| 2 | 10 | 5 | — | — |
| 3 | 15 | 10 | — | — |
| 4 | 20 | 15 | 5 | 5 |
RELATION BETWEEN DIAL NUMBER AND POSITION $L_1$ (mm) OF IRRADIATION
| DIAL NUMBER FRONT SIDE \ REAR SIDE DIAL NUMBER | 1 | 2 | 3 | 4 |
|---|---|---|---|---|
| 1 | 3 | — | — | — |
| 2 | 6 | 9 | — | — |
| 3 | 9 | 12 | 15 | — |
| 4 | 12 | 15 | 18 | 21 |

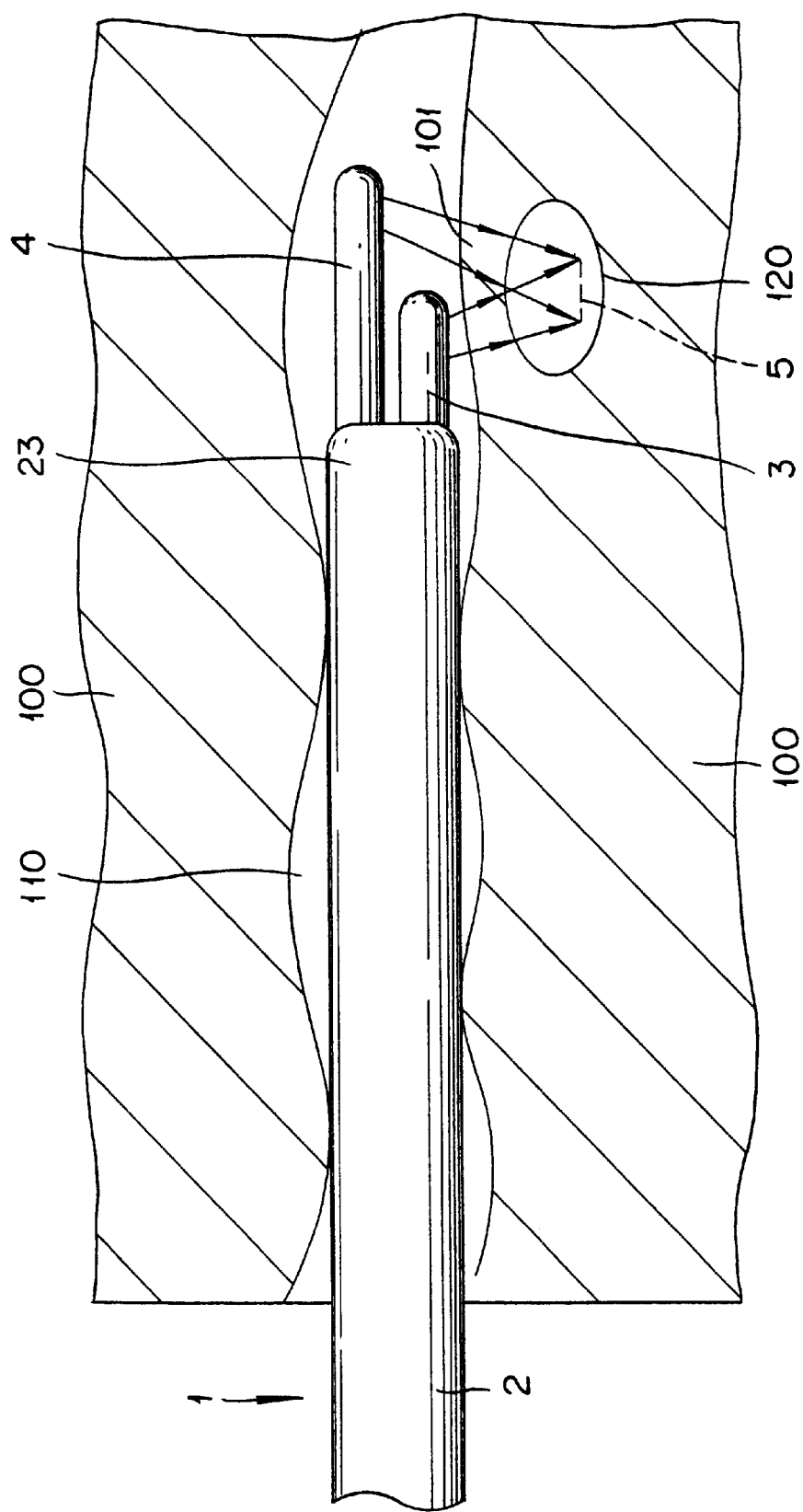

LASER IRRADIATION DEVICE AND METHOD FOR THERAPY OF PROSTATE GLAND BY USE THEREOF

BACKGROUND OF THE INVENTION

1. Field of the Invention

This invention relates to a lateral-irradiation type laser irradiation device for curing ailing tissue by irradiating the affected region with a laser beam and a method for the therapy of prostate gland by the use of the laser irradiation device.

2. Description of the Prior Art

Some kinds of the laser irradiation device is used for curing an ailing tissue by inserting the device into a lumen such as the blood vessel, the urogenital canal, or the abdominal cavity and causing the device to emit an in-vivo deep reaching laser beam to the affected region.

This laser irradiation device, by making use of a relevant body cavity or by being inserted into a relevant part of the body through a small incision, cures a lesion by irradiating a laser beam of a varying energy density upon the site of the lesion thereby inducing degeneration, necrosis, solidification, cauterization, incision, or transpiration of the lesion.

This technique consists in directly irradiating the laser beam on the lesion located in or near the surface layer of the tissue. Recently it has become to be utilized also for curing a lesion located in the deep part of the tissue.

Since the laser beam is emitted at a relatively high output for the purpose of heating the lesion of this sort to an amply high temperature, it has the possibility of injuring the relevant surface layer of the tissue.

In the circumstance, therefore, an idea of providing the laser irradiation device at the distal end part thereof with a plurality of laser beam emitting parts and causing these emitting parts respectively to emit laser beams in a pattern so divided that the laser beams may overlap on the site of lesion is conceivable. This modified laser irradiation device can allay the injury of the surface layer to a certain extent and heat the site of lesion to a sufficiently high temperature because it prevents a laser beam of unduly high output from impinging on the surface layer.

The laser irradiation device of this construction, however, allows no easy control of the depth of the position at which the laser beams emitted from the different laser emitting parts are converged (beam-condensing position). It, therefore, entails such problems as disabling application of uniform heat to the whole of the lesion, giving rise to local overheating or unduly insufficient heating, suffering the lesion to cause pain to the patient or involve complication, failing to manifest a fully satisfactory curing effect, and tending to incur relapse of the disease.

Further, this device by nature inevitably fixes the depth of the beam-condensing position at a constant distance. To change the depth of beam-condensing position to a necessary depth, therefore, it requires to exchange the laser irradiating device (laser probe) for a spare part having the depth of the beam-condensing position set in advance to the necessary distance.

When the depth of the beam-condensing position is altered by the exchange of the laser irradiation device, this alteration of the depth is barely attained stepwise and further brings such flaws as complicating the operation and increasing the load on the patient.

SUMMARY OF THE INVENTION

This invention, conceived in the light of the true state of prior art mentioned above, has for the object thereof the provision of a lateral-irradiation type laser irradiation device which is capable of effectively irradiating a target site (particularly at a considerable depth) with a laser beam while infallibly and easily preventing normal tissue from injury and a method for curing prostate gland by the use of the laser irradiation device.

According to this invention, since the laser beams emanating from a plurality of emitting parts are converged (condensed) via different routes on a target position and the energy densities of these laser beams are heightened at the target position and in the neighborhood thereof, the target site can be heated to a necessary temperature and the site (normal tissue) other than the target site can be held at a relatively low temperature. As a result, the injury possibly inflicted on the site other than the target site can be precluded completely or allayed markedly and, in particular, the safety of the patient can be secured.

According to this invention, since the target position can be moved by an emitting direction changing means, the whole of the target site can be uniformly heated to a necessary temperature while the site other than the target site is easily and infallibly retained at a relatively low temperature. Further, since the depth of the target position can be changed to an arbitrarily selected distance without requiring exchange of the laser irradiation device, the operation can be facilitated and the load on the patient can be alleviated.

Even when the inserting part of the laser irradiation device is barely capable of advancing halfway along the distance to a given body cavity, the device can heat the target site to a necessary temperature by irradiating the target site with laser beams. When the target site allows no easy transmission of laser beams or the laser beams for the irradiation have relatively low energy densities, the laser irradiation device is capable of irradiating the target site with laser beams while avoiding the site liable to involve complication.

According to the method of this invention, the inserting part of the laser irradiation device can be inserted from outside the body into a long slender lumen and the laser beams issued from a plurality of emitting parts can be passed through different routes and converged (condensed) on a target position and the energy densities of these laser beams can be heightened at the target position and in the neighborhood thereof. In the therapy of prostate gland, a disease in which a lesion exists at the end of a slender long urogenital canal, therefore, the method of this invention is highly effective in performing easily the therapy without exposing the patient to an undue load while precluding infliction of injury on the site other than the target site.

BRIEF DESCRIPTION OF THE DRAWINGS

FIG. 2 is a cross section of a necessary portion illustrating the distal end part of the laser irradiation device, FIG. 3A is a schematic cross section taken through FIG. 2 along the line IIIA—IIIA, FIG. 3B is a schematic cross section taken through FIG. 2 along the line IIIB—IIIB, FIG. 3C are tables showing the relations between the dial numbers of the adjusting parts on the one part and the depths of irradiation and the positions of irradiation on the other hand, FIG. 4 is a side view illustrating a necessary portion of the state in witch the laser irradiation device is inserted into a body cavity.

DETAILED DESCRIPTION OF THE PREFERRED EMBODIMENT

Now, the laser irradiation device of this invention will be described in detail below based on preferred embodiments illustrated in the annexed drawings.

<<Embodiment 1>>

Figure 1:
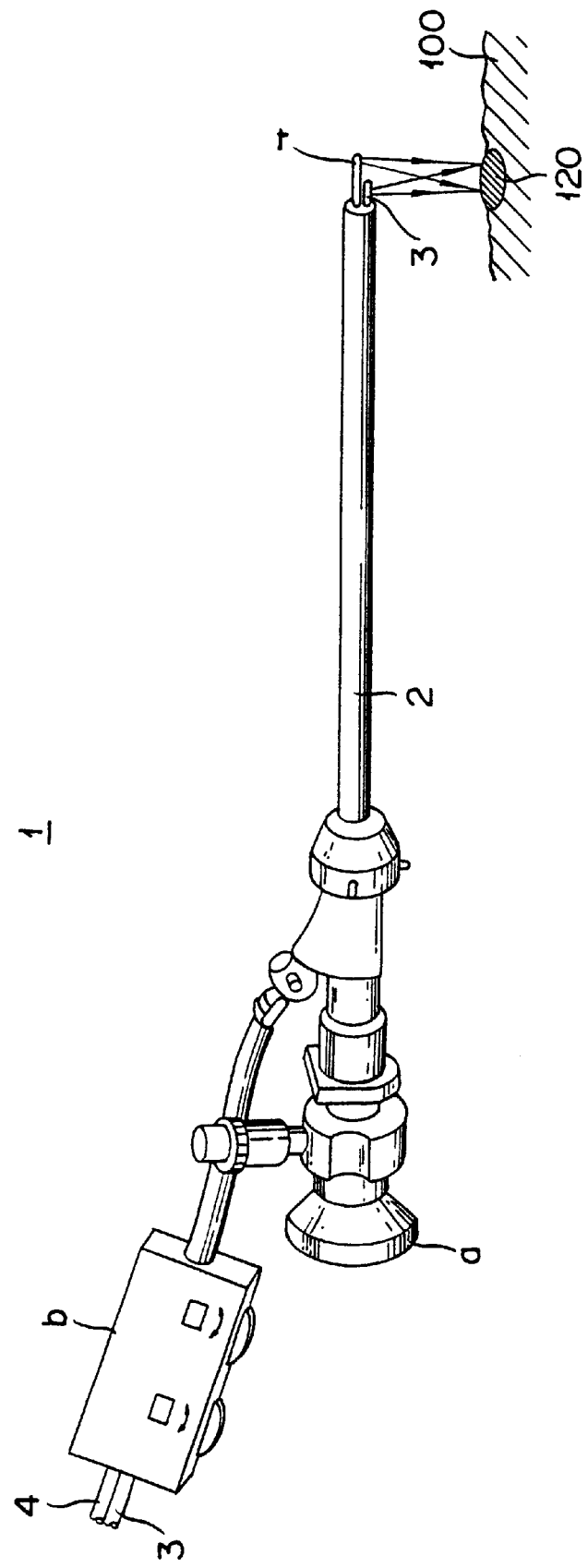
FIG. 1 is a schematic perspective view illustrating a laser irradiation device according to Embodiment 1 of this invention.

With reference to FIG. 1, a laser irradiation device 1 is a lateral-irradiation type laser irradiation device which is provided in an elongate sheath (main body) 2 thereof with laser probes 3 and 4 disposed parallel to each other and adapted to emit laser beams capable of reaching depths in an organism toward a tissue 100. In FIG. 1, the symbol "a" denotes an eye-piece part and the symbol "b" an adjusting part for adjusting the distal end position of the laser probes 3, 4.

In the sheath 2 of the laser irradiation device 1, working lumens (hollow parts) 21 and 22 both opened respectively at the distal end and the proximal end are formed as illustrated in FIG. 2. These working lumens are respectively parallel to the longitudinal axis of the sheath 2. Here, the right side in the bearings of the drawing is regarded as the "distal end" and the left side as the "proximal end" (this relationship will similarly apply hereinafter).

The laser probe 3 is disposed in the working lumen 21 and the laser probe 4 in the working lumen 22 respectively movably in the longitudinal direction of the sheath 2. The disposition of the laser probes 3 and 4 in the movable state results in constructing an emitting direction changing means which changes the directions of emission of laser beams as will be described specifically herein below. This system constitutes itself a very simple means for changing directions of emission. On the proximal end sides of these laser probes 3 and 4, a laser generating device (not shown) adapted to generate laser beams is disposed.

The laser probe 3 mentioned above is composed of an optical fiber (light-guiding member) 31 and a reflecting mirror (emitting part) 32 having a rounded leading terminal disposed in the distal end part of the optical fiber 31 and the laser probe 4 mentioned above is composed of an optical fiber (light-guiding member) 41 and a reflecting mirror (emitting part) 42 disposed in the distal end part of the optical fiber 41.

The optical fibers 31 and 41 are each formed of a core and a clad disposed in the outer peripheral part of the core so as to encircle the core and having a refractive index lower than that of the core. The diagram avoids placing a hatch for depicting a cross section in the optical fibers 31 and 41 for fear that it may obscure a light path (this rule will similarly apply hereinafter).

These optical fibers 31 and 41 do not need to submit to any particular restriction but require only to be capable of guiding laser beams. Their cores, for example, may have quartz as a main component thereof or may be formed of either a multi-component glass or a resin of acrylic origin. The clad mentioned above imposes no particular restriction but only requires to have a lower refractivity than the core. Further, these optical fibers may be composed of either one core or a plurality of cores arrayed within a clad. Alternatively, the optical fibers may be in the form of an optical fiber bundle which is obtained by bundling a plurality of optical fibers.

The reflecting mirrors 32, 42 mentioned above constitute themselves emitting means for issuing laser beams.

The laser probes 3, 4 are disposed parallel in the vertical direction as illustrated in FIG. 2 and FIG. 3. The laser probe 4 is positioned above the laser probe 3 and the distal end part (reflecting mirror 42) of the laser probe 4 is positioned forward from the distal end part (reflecting mirror 32) of the laser probe 3.

The various conditions such as angle of the reflecting mirror 32 are so set that, when the laser is viewed from the front, the reflecting mirror 32 may emit the laser beam downward, namely in the direction in which the laser probes 3 and 4 form a line and, when the laser irradiation device 1 is viewed from the side, the reflecting mirror 32 may emit the laser beam in a direction inclined toward the distal end side as illustrated in FIG. 2.

The various conditions such as angle of the reflecting mirror 42 are so set that, when the laser is viewed from the front, the reflecting mirror 42 may emit the laser beam downward, namely in the direction in which the laser probes 3 and 4 form a line and, when the laser irradiation device 1 is viewed from the side, the reflecting mirror 42 may emit the laser beam in a direction inclined toward the proximal end side as illustrated in FIG. 2.

As a result, the laser beam emitted from the laser probe 3 and the laser beam emitted from the laser probe 4 overlap at a fixed position on the lower side as illustrated in FIGS. 1, 2.

In the present specification, the position at which the laser beams overlap (coincide) will be referred to as a "target position."

The laser beams to be used do not need to submit to any particular restriction but requires only to be capable of reaching a depth in an organism. They properly have a wavelength in the approximate range of 700–1300 nm, preferably 800–900 nm. The laser beams of this wavelength are not easily absorbed by the water component of the tissue. When they irradiate the tissue, they induce absorption of energy only sparingly in the surface layer part and exhibit an ability to impinge effectively on the target part (lesion) 120 located at a depth in the tissue.

As concrete embodiments of the laser beam generating device for generating the laser beams of the wavelength mentioned above, gaseous lasers such as the He-Ne laser, solid lasers such as the Nd-YAG laser, and semiconductor lasers such as the GaAlAs laser may be cited.

The outside diameter (diameter) of the inserting part of the laser irradiation device 1 does not need to submit to any particular restriction but requires only to be enough to allow insertion of the inserting part into a body cavity 110. The outside diameter of the sheath 2 properly is in the approximate range of 2–20 mm, for example, preferably in the approximate range of 3–8 mm.

As concrete examples of the material for the formation of the sheath 2, polyolefins such as polyethylene and polypropylene, polyesters such as ethylene-vinyl acetate copolymer (EVA), polyvinyl chloride, polyethylene terephthalate, and polybuthylen terephthalate, polyamide, polyurethane, polystyrene, fluoroplastic, polymer alloys containing one of the compounds mentioned above, and combinations of two or more such compounds may be cited.

The adjusting part 50, as illustrated in FIG. 3A, is possessed of adjusting dials 53 and 54 which partly protrude from the lateral part of a case 51. While these adjusting dials 53, 54 are rotatably attached to the case 51, they nip the laser probes 3, 4 in cooperation with a plurality of guide rollers 55 inside the case 51. The adjusting part 50 is so constructed that the laser probes 3, 4 may be advanced forward or backward in the axial direction by suitably rotating the adjusting dials 53, 54 normally or reversely.

Since the adjusting part 50 prefers the construction thereof to allow inspection of the amount of the advance of the laser probes, the present embodiment opens a window 56 in the upper side of the case 51 and enables the dial numbers inscribed in the upper sides of the adjusting dials 53, 54 to be seen by an observer through this window 56.

The adjusting dials 53, 54 prefer to have inscribed on the outer peripheral faces thereof antislip knurls which are adapted to ensure and facilitate the motion of the laser probes 3, 4 to a greater extent.

The dial numbers may be arbitrarily selected. For example, the letters "1," "2," "3," and "4" are affixed at angular intervals of 90 degrees on each of the adjusting dials 53, 54 and these dial numbers are used as a measure of the amount of motion of the laser probes 3, 4.

This measure of the amount of motion is illustrated in FIG. 3C. To be specific, when the dial number changes from "1" to "2," the laser probes 3, 4 are moved over a distance of about 6 mm ($10/\sqrt{3}$ mm) in the axial direction. The angles of inclination of the reflecting mirrors 32, 42 relative to the optical axis are 30 degrees. In FIG. 3C, however, the numerical values are partly missing because the distal end part of the laser probe 4 cannot be positioned in any state on the forward side from the distal end part of the laser probe 3.

Now, the operation of Embodiment 1 will be described below.

For a start, the sheath 2 is inserted as guided by the distal end part 23 thereof into the body cavity 110 until the distal end part 23 is positioned near the target part 120 to be irradiated (on the nearer side in the direction of advance) as illustrated in FIG. 4.

Then, the laser probes 3, 4 are inserted respectively into the working lumens 21 and 22 and the distal end parts of the laser probes 3, 4 are allowed to protrude in a fixed amount from the distal end of the sheath 2. In this case, the laser probe 4 and the laser probe 3 are so arranged that the distal end part of the former probe may fall on the forward side from the distal end part of the latter probe as illustrated in FIG. 4.

Optionally, the laser irradiating device 1 having the laser probes 3, 4 inserted in advance respectively into the working lumens 21, 22 may be inserted instead into the body cavity 110.

Then, the laser irradiating device 1 is adjusted so that the target position (coinciding position) 5 may assume a required position in the target part 120.

The adjustment of the target position 5 in the direction perpendicular to the longitudinal axis of the sheath 2 (in the vertical direction in the bearings of the diagram) is accomplished by moving either or both of the laser probes 3, 4 in a required direction (the longitudinal direction of the sheath 2) relative to the sheath 2 thereby adjusting the distance between the reflecting mirrors 32 and 42.

The target position 5 is separated from the laser probes 3, 4 when the distance between the reflecting mirrors 32 and 42 is elongated. Conversely, the target position 5 approaches the laser probes 3, 4 when the distance between the reflecting mirrors 32 and 42 are shortened.

The adjustment of the target position 5 in the longitudinal direction of the sheath 2 is accomplished by either moving the laser irradiating device 1 wholly in the longitudinal direction or moving the laser probes 3, 4 in the longitudinal direction while keeping the reflecting mirrors 32 and 42 at a fixed distance. This adjustment allows an alteration of the direction of emission.

By moving the laser probes 3, 4 relative to the sheath 2 thereby adjusting the target position 5, the burden on the patient under treatment can be alleviated and the operation can be facilitated because the sheath 2 does not need to be moved.

The adjustment of the target position 5 in the circumferential direction of the sheath 2 is accomplished by rotating the laser irradiating device 1 wholly round the longitudinal axis as the center. This adjustment likewise allows an alteration of the direction of emission.

To be specific, the laser probe 4 and the laser probe 3 are so laid out by way of initial setting that the distal end part of the former probe may fall about 6 mm, for example, forward from the distal end part of the latter probe. This state occurs in the present embodiment when the dial number on the adjusting dial 53 on the front side (hereinafter referred to as "front side dial") is "1" and the dial number on the adjusting dial 54 on the rear side (hereinafter referred to as "rear side dial") is "1."

Then, the sighting is performed. The laser irradiating device 1 is so adjusted that the irradiation effected by this laser irradiating device 1 may reach the prescribed depth D1 over the prescribed distance L1, providing that D1 stands for the target depth of the target position 5 and L1 for the distance from the distal end position of the laser probe 3 to the central position of irradiation of the target position 5 as illustrated in FIG. 2.

This adjustment is carried out based on the dial numbers (1, 2, 3, and 4) inscribed on the upper faces of the adjusting dials 53, 54 as the measure. In the present embodiment, the motion is made in an increment of about 6 mm each time the dial number produces a change of 1. Optionally, the adjusting dials 53, 54 may be stopped halfway between adjacent dial numbers.

After this adjustment, the laser beam generating device (not shown in the diagram) is actuated to start injection of the laser beams respectively through the proximal end parts of the laser probes 3, 4. The laser beam entering the laser probe 3 is guided by the optical fiber 31 from the proximal end part through the distal end part, reflected by the reflecting mirror 32, and irradiated on the target position 5 and the laser beam entering the laser probe 4 is guided by the optical fiber 41 from the proximal end part through the distal end part, reflected by the reflecting mirror 42, and irradiated on the target position 5.

That is to say, the laser beam reflected by the reflecting mirror 32 and the laser beam reflected by the reflecting mirror 42 are passed through different routes and converged at the target position 5. As a result, the target position 5 and the neighborhood thereof in the tissue 100 are heated by the laser beams to a required temperature.

Meanwhile, the site above the target part 120 (such as, for example, a surface layer part 101 of the tissue 100) and the site thereunder are respectively retained respectively at relatively low temperatures because the laser beam reflected by the reflecting mirror 32 and the laser beam reflected by the reflecting mirror 42 do not overlap therein.

Then, by moving the target position 5, namely by changing continuously the target position 5 by the use of a means for altering the direction of emission, the directions of emission of the laser beams are altered and the target part 120 is wholly heated to a required temperature.

Figure 5:
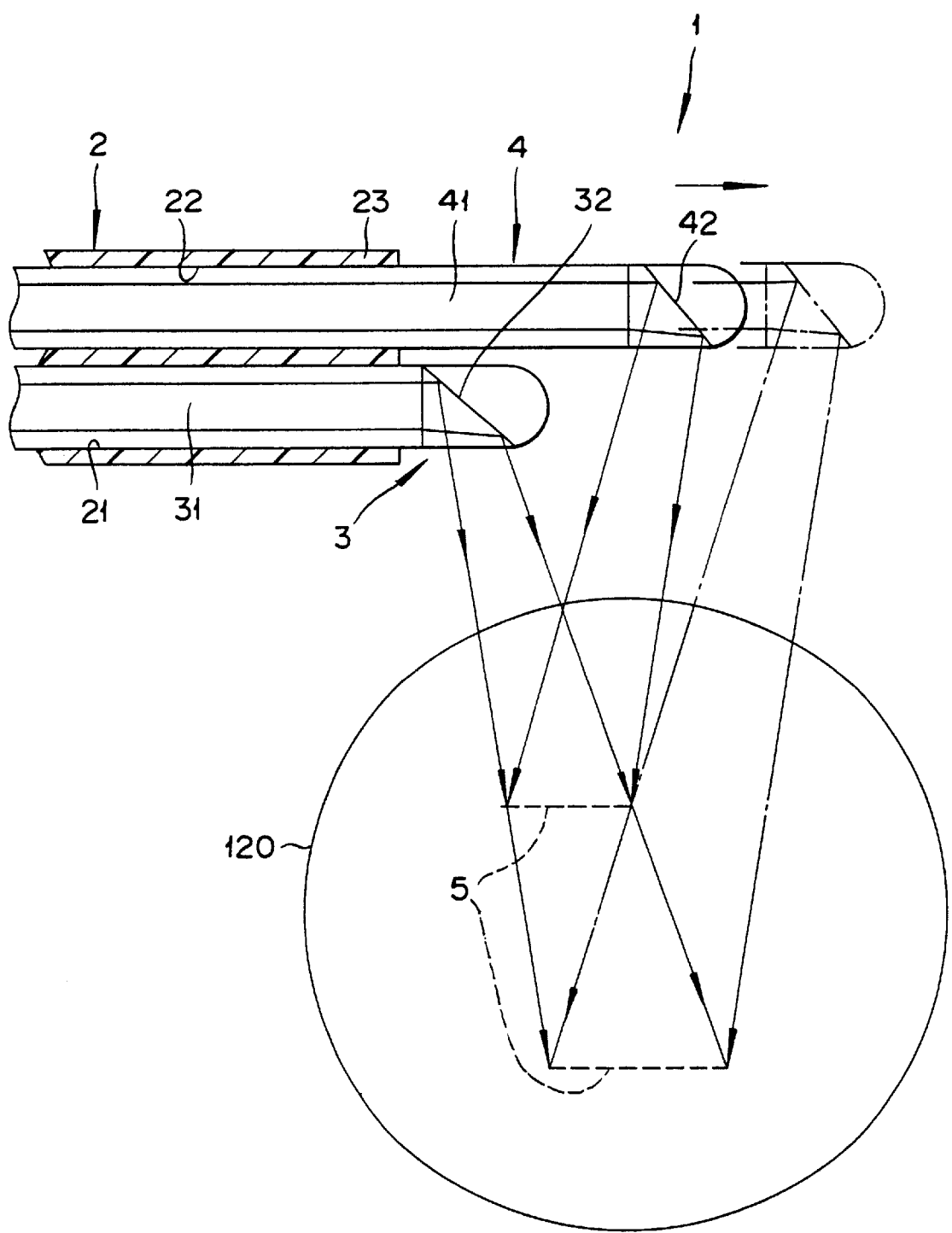
FIG. 5 is across section illustrating a necessary portion of the case of vertically moving the target position of the laser irradiation device.

For example, the interval between the reflecting mirrors 32 and 42 is elongated and the target position 5 is moved downward when the laser probe 4 is moved to the right side as indicated by an alternate long and short dash line in the diagram while the laser probe 3 is kept in a fixed state as illustrated in FIG. 5. Conversely, the interval between the reflecting mirrors 32 and 42 is shortened and the target position 5 is moved upward in the bearings of the diagram when the laser probe 4 is moved to the left in the diagram while the laser probe 3 is kept in a fixed state.

Figure 6:
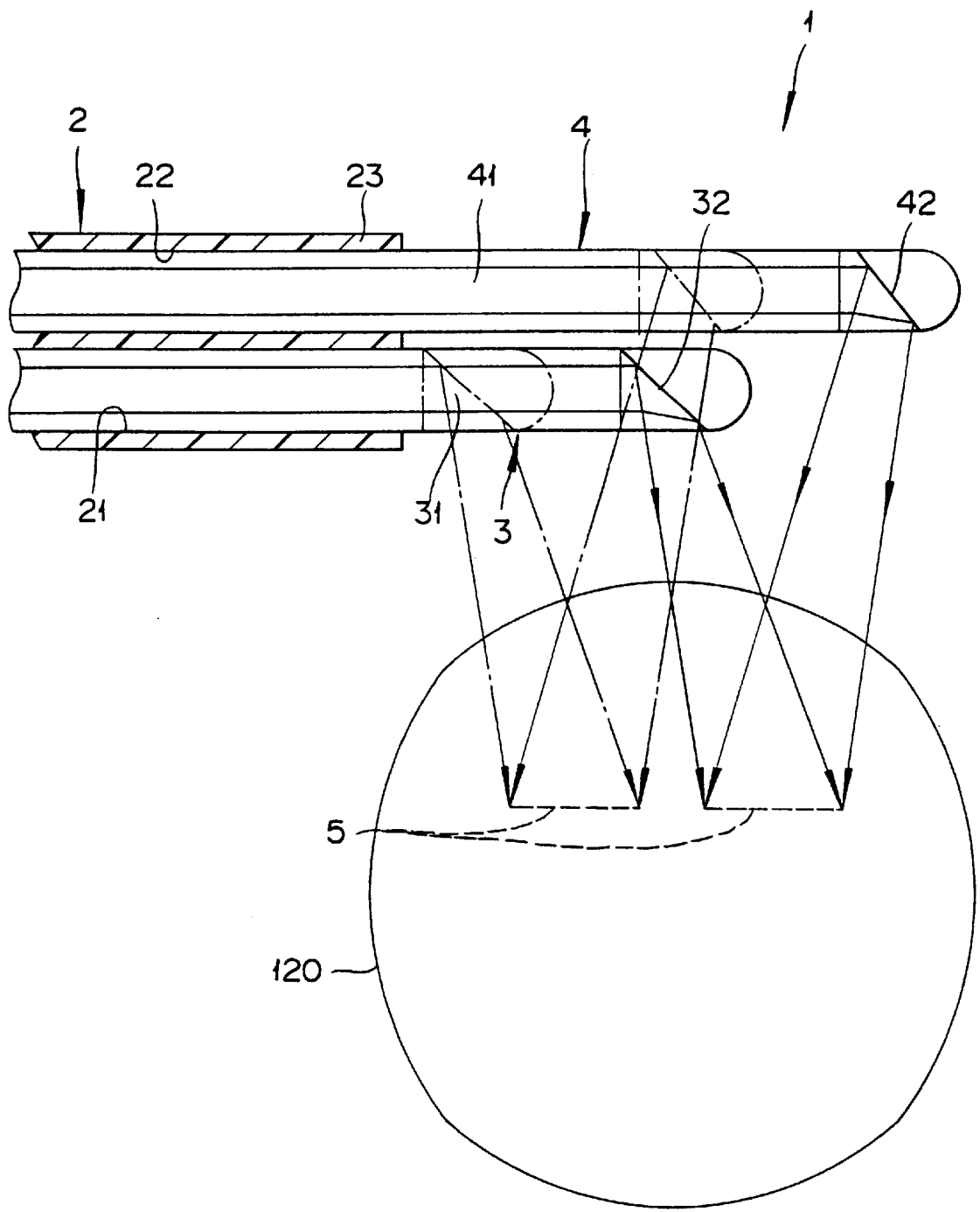
FIG. 6 is a cross section illustrating a necessary portion of the case of laterally moving the target position of the laser irradiation device.

In the case of moving the target position 5 in the longitudinal direction of the sheath 2, for example, the target position 5 is moved to the right side when the laser probes 3, 4 are moved to the right side from the state of the alternate long and short dash line to the state of the solid line while the interval between the reflecting mirrors 32 and 42 is kept at a fixed length as illustrated in FIG. 6. Conversely, the target position 5 is moved to the left side when the laser probes 3, 4 are moved to the left side from the state of the solid line to the state of the alternate short and long dash line while the interval between the reflecting mirrors 32 and 42 is kept at a fixed length. Again in this case, when the target position 5 is adjusted by moving the laser probes 3, 4 relative to the sheath 2, the burden on the patient can be alleviated and the operation can be facilitated because the sheath 2 does not need to be moved.

Figure 7:
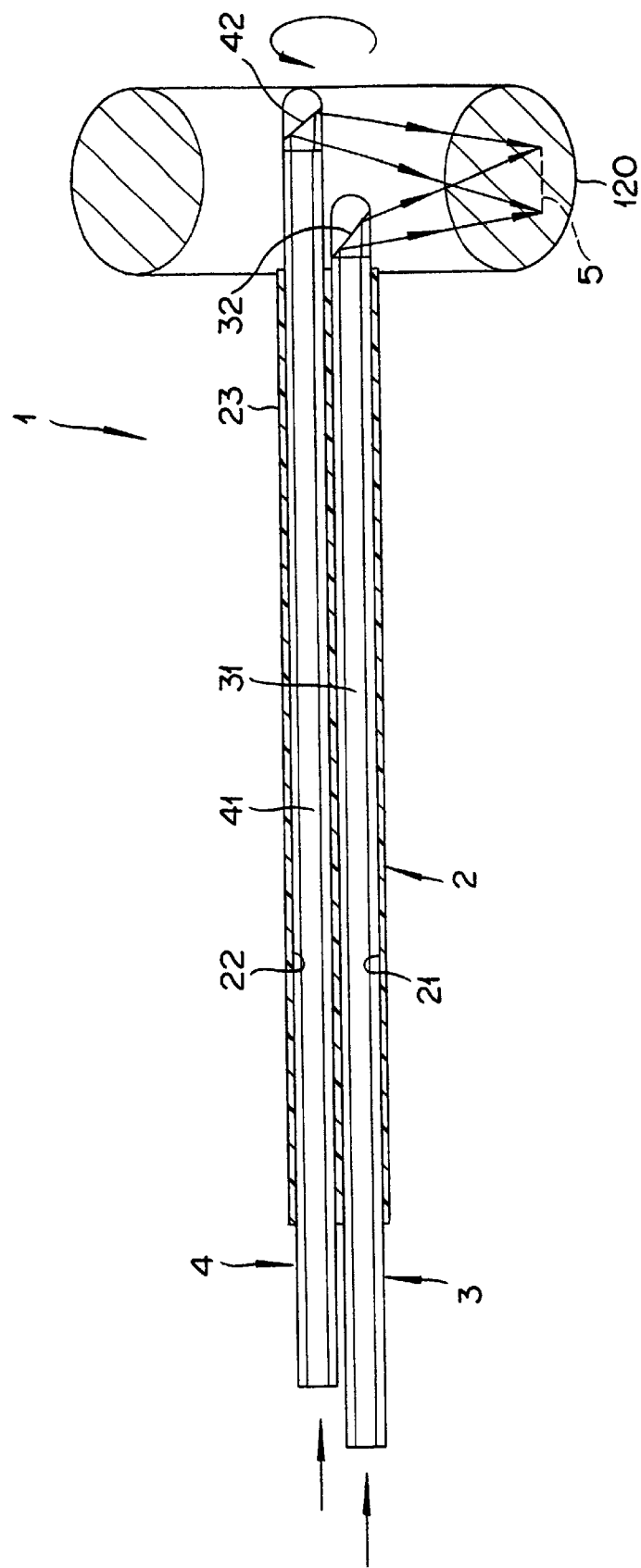
FIG. 7 is a cross section illustrating a necessary portion of the case of circumferentially moving the target position of the laser irradiation device.

In the case of moving the target position 5 in the circumferential direction of the sheath 2, for example, the target part 120 in a circular shape can be wholly heated to a necessary temperature by rotating wholly the laser irradiating device 1 either clockwise or counterclockwise round the longitudinal axis of the sheath 2 as the center as illustrated in FIG. 7.

When the irradiation of the target part 120 with the laser beams which is performed while the target position 5 is suitably moved in the vertical direction, longitudinal direction, or circumferential direction and the direction of emission is altered by the use of the means for altering the direction of emission as described above is completed, the laser irradiating device 1 is wholly extracted from within the body cavity 110.

In accordance with the present Embodiment 1, the site (normal tissue) other than the target part 120 can be retained at a relatively low temperature because the laser beams reflected by the reflecting mirrors 32 and 42 are passed through different paths and concentrated (converged) at the target position 5 during the irradiation of the target part 120 with the laser beams. As a result, the otherwise possible infliction of an injury on the site other than the target part 120 can be precluded and the safety of the patient can be heightened. The injury on the surface layer part 101 can be prevented even when the target part 120 is located at a particularly large depth.

Since the laser beams from the reflecting mirrors 32, 42 are concentrated at the target position 5, the energy densities of the laser beams are heightened at the target position 5 and in the neighborhood thereof and consequently the target part 120 can be heated to a necessary temperature.

In the present Embodiment 1, since the target position 5 can be moved in an arbitrary direction, the target part 120 which is located at an arbitrary position and is possessed of an arbitrary shape and an arbitrary size can be easily and infallibly heated uniformly throughout to a necessary temperature and can be prevented from being locally heated excessively or insufficiently.

For example, since the target position 5 can be moved in a direction perpendicular to the longitudinal axis of the sheath 2 by varying the interval between the reflecting mirrors 32 and 42, the operation can be facilitated and the burden on the patient can be alleviated without requiring the laser irradiating device to be exchanged for the purpose of changing the depth of the target position 5.

In the present invention, the laser beams to be issued from the distal end parts of the laser probes 3, 4 may be selected arbitrarily from among divergent rays, collimated rays, and convergent rays. It is, however, preferable to use collimated rays or convergent rays.

When the laser beams issued from the distal end parts of the laser probes 3, 4 are collimated rays or convergent rays, the laser beams can be concentrated at the target position 5 and the energy densities of the laser beams can be heightened at the target position 5 and in the neighborhood thereof. In other words, in the case of the collimated rays or convergent rays, when the energy densities of the laser beams irradiating the target position 5 are fixed, the energy densities of the laser beams irradiating the surface layer part 101 can be lowered and the injury on the surface layer part 101 can be prevented with clear infallibility as compared with the case of the divergent rays.

When the laser beams emitted from the distal end parts of the laser probes 3, 4 are convergent rays, the laser beams are preferred to converge at the target position 5, namely the position at which the laser beams converge (the position at which the spot lights of the laser beams formed on a face perpendicular to the optical axis occupy the smallest areas) is preferred to coincide with the target position 5. The convergence of the laser beams at the target position 5 is effective in heightening the energy densities of the laser beams at the target position 5 and in the neighborhood thereof.

For the purpose of enabling the laser beams issued from the distal end parts of the laser probes 3, 4 to form collimated rays or convergent rays, an optical system for transforming laser beams into collimated rays or convergent rays is installed in the light paths of the laser beams. In this case, the optical systems mentioned above may be installed separately from the reflecting mirrors 32, 42 or the reflecting mirrors 32, 42 may be adapted to serve concurrently as the optical systems.

When the reflecting mirrors 32, 42 are required to serve concurrently as the optical systems mentioned above, it suffices just to impart a concave shape to the reflecting faces of the reflecting mirrors 32, 42.

When the optical systems for transforming the laser beams into collimated rays or convergent rays are not installed, the use of optical fibers having a small numerical aperture brings an effect approximating closely to the generation of collimated rays. In this case, the numerical aperture is properly not more than 0.4, preferably not more than 0.3.

This invention does not particularly discriminate the working lumens 21, 22 of the sheath 2 or the laser probes 3, 4 on account of sectional form. When the working lumens 21, 22 of the sheath 2 are given a noncircular sectional form, for example, the laser probes 3, 4 are preferred to have a sectional form which corresponds to the sectional form of the working lumens 21, 22 mentioned above. This correspondence prevents the laser probes 3, 4 from being twisted or turned and consequently suffered to obstruct the concentration at the target position 5 of the laser beams emitted from the distal end parts of the laser probes 3,4. In other words, the correspondence enables the laser beams issued from the distal end parts of the laser probes 3, 4 to be concentrated at the target position 5 with enhanced infallibility.

In this invention, the laser beams issued from the component emitting parts may be equal or different in quantity. When the laser beams emanating from the component emitting parts are equalized in quantity of light, the safety of the laser beams for the patient is heightened because the temperature of the surface layer part can be lowered for the fixed total quantity of light of the laser beams from the component emitting parts.

In this invention, the number of emitting parts of the irradiating means, namely the number of laser probes, does not need to be limited to 2 but may be increased to 3 or more. Since an unduly large number of emitting parts brings complication of the construction of the irradiating means, the proper number or emitting parts is in the approximate range of 2–6, preferably in the approximate range of 2–4.

<<Embodiment 2 >>

Figure 8:
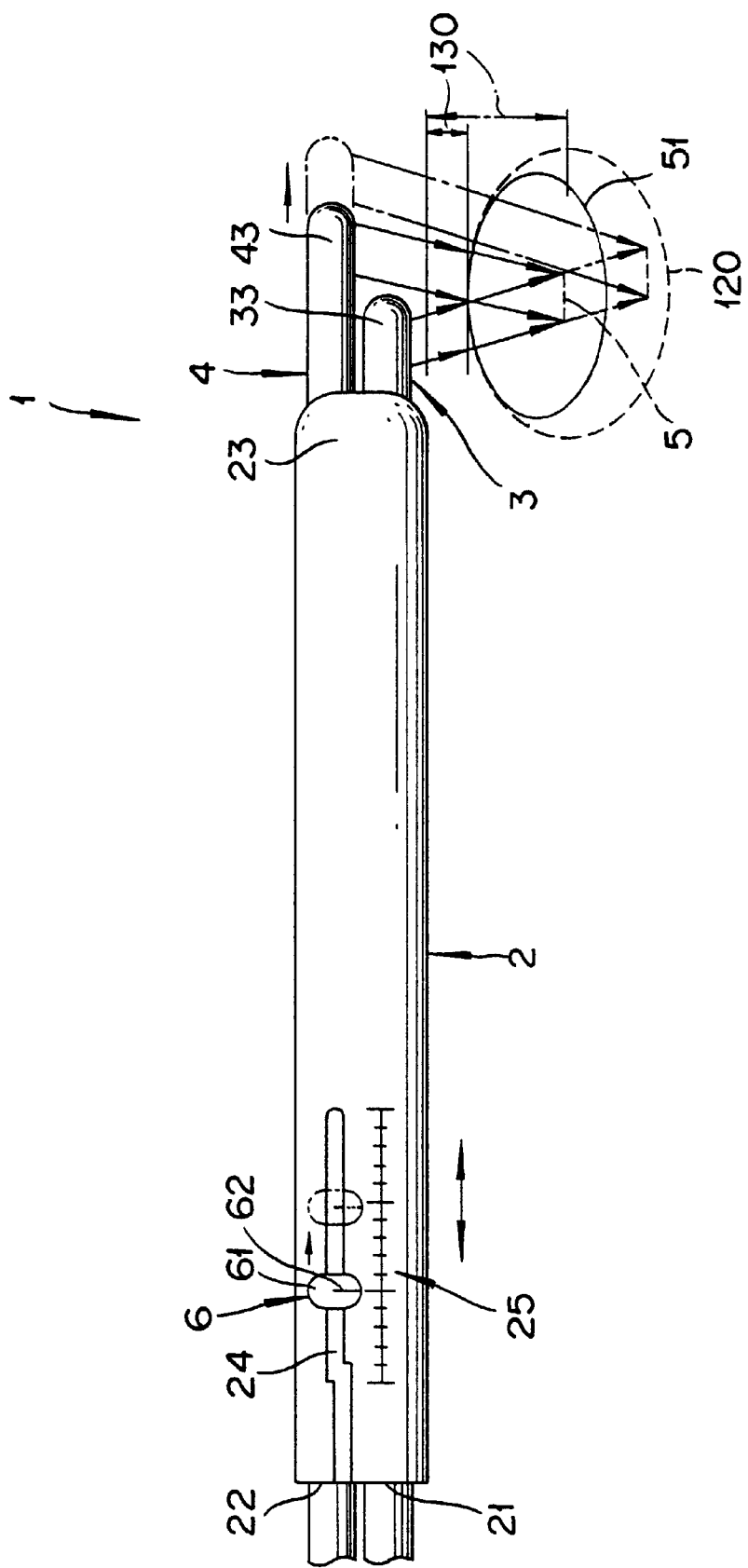
FIG. 8 is a side view illustrating a necessary portion of a laser irradiation device according to Embodiment 2 of this invention.

FIG. 8 is a side view illustrating Embodiment 2 of the laser irradiating device of this invention. The component parts which are shared by this Embodiment 2 and the preceding Embodiment 1 will be omitted from the following description. The main points of difference between the two embodiments in question will be described below.

In the laser irradiating device 1 which is illustrated in the diagram, the laser probe 3 is installed as fixed to the sheath 2, the laser probe 4 is installed as allowed to move in the longitudinal direction of the sheath 2, and the laser probe 4 is provided with a lever 6 as a means for altering the direction of emission and producing an operation of moving the laser probe 4.

The laser probes 3, 4 may be moved by the use of the adjusting parts which are illustrated in FIGS. 1–3. When either of the two laser probes is used alone as in the present embodiment, it is favorable to use the lever with a view to simplifying the operation.

This lever 6 is composed of a head part 61 and a shank (not shown) smaller in diameter than the head part 61. The head part 61 is provided with a linear index 62.

On the proximal end side of the sheath 2, a long hole 24 for guiding the lever 6 mentioned above is formed. This long hole 24 is opened at the proximal end and in the outer periphery of the sheath 2 and is made to communicate with the working lumen 22. This long hole 24 is formed parallel to the longitudinal axis of the sheath 2 and has a width (the length in the vertical direction in the bearings of FIG. 8) larger than the outside diameter (diameter) of the axial part of the lever 6 and smaller than the head part 61.

The shank of the lever 6 mentioned above is inserted in the long hole 24. The head part 61 is positioned on the outer peripheral side of the sheath 2. Near the long hole 24 on the outer peripheral surface of the sheath 2, a graduated scale 25 is disposed parallel to the longitudinal axis of the sheath 2, namely to the long hole 24.

The graduated scale 25 corresponds to the positions of the emitting part 43, namely to the intervals between an emitting part 33 of the laser probe 3 and the emitting part 43 of the laser probe 4. By reading the value of the graduated scale 25 which coincides with the index 62 of the lever 6, therefore, the distance between the target position 5 in the direction perpendicular to the longitudinal axis of the sheath 2 and the outer peripheral face of the sheath 2 (the surface of the tissue), namely, the depth of the target position 5, can be comprehended from the value.

Then, the operation of Embodiment 2 will be described below.

When the operator grips the head part 61 of the lever 6 and imparts a motion to the lever 6, the lever 6 slides along the long hole 24 and, in concert with this slide, the laser probe 4 moves in the longitudinal direction of the sheath 2 and produces a change in the interval between the emitting part 33 and the emitting part 43.

In the state indicated by the solid line in FIG. 8, the target position 5 and the neighboring site (region) 51 are heated to a necessary temperature. When the lever 6 is moved to the right side until the state indicated by the alternate short and long dash line is assumed, the laser probe 4 is also moved to the right side cooperatively with the motion of the lever 6, with the result that the interval between the emitting parts 33 and 43 will be elongated and the target position 5 will be moved downward.

By the fact that the motion of the lever 6 alters the direction of emission of the laser beam and moves the target position 5 in the manner described above, the target part 120 can be wholly heated uniformly to the necessary temperature.

Conversely, when the lever 6 is moved to the left side from the state indicated by the alternate short and long dash line, the laser probe 4 is also moved to the left side cooperatively with the motion of the lever 6, with the result that the interval between the emitting parts 33 and 43 will be shortened and the target position will be moved upward.

In FIG. 8, a range 130 above the site 51 is the region to be retained at a relatively low temperature (the region to be kept warm). This range 130 is enlarged by the motion of the lever 6 to the right.

While the present Embodiment 2 produces the same effect as the Embodiment 1, the Embodiment 2 is particularly capable of facilitating the motion of the laser probe 4 because it is provided with the lever 6 as a means for altering the direction of emission.

Further, the depth of the target position 5 can be easily and infallibly transformed into the depth of the target because the depth of the target position 5 can be comprehended from the value of the graduated scale 25 which coincides with the index 62 of the lever 6. As a result, the target part 120 can be wholly heated easily and infallibly at the necessary temperature while the site other than the target part 120 is kept at a relatively low temperature.

This invention does not need to be limited to the embodiments cited above. Optionally, the laser probes 3, 4 may be adapted to be moved independently of each other in the longitudinal direction relative to the sheath 2 and may be each provided with the lever 6 mentioned above.

<<Embodiment 3>>

Figure 9:
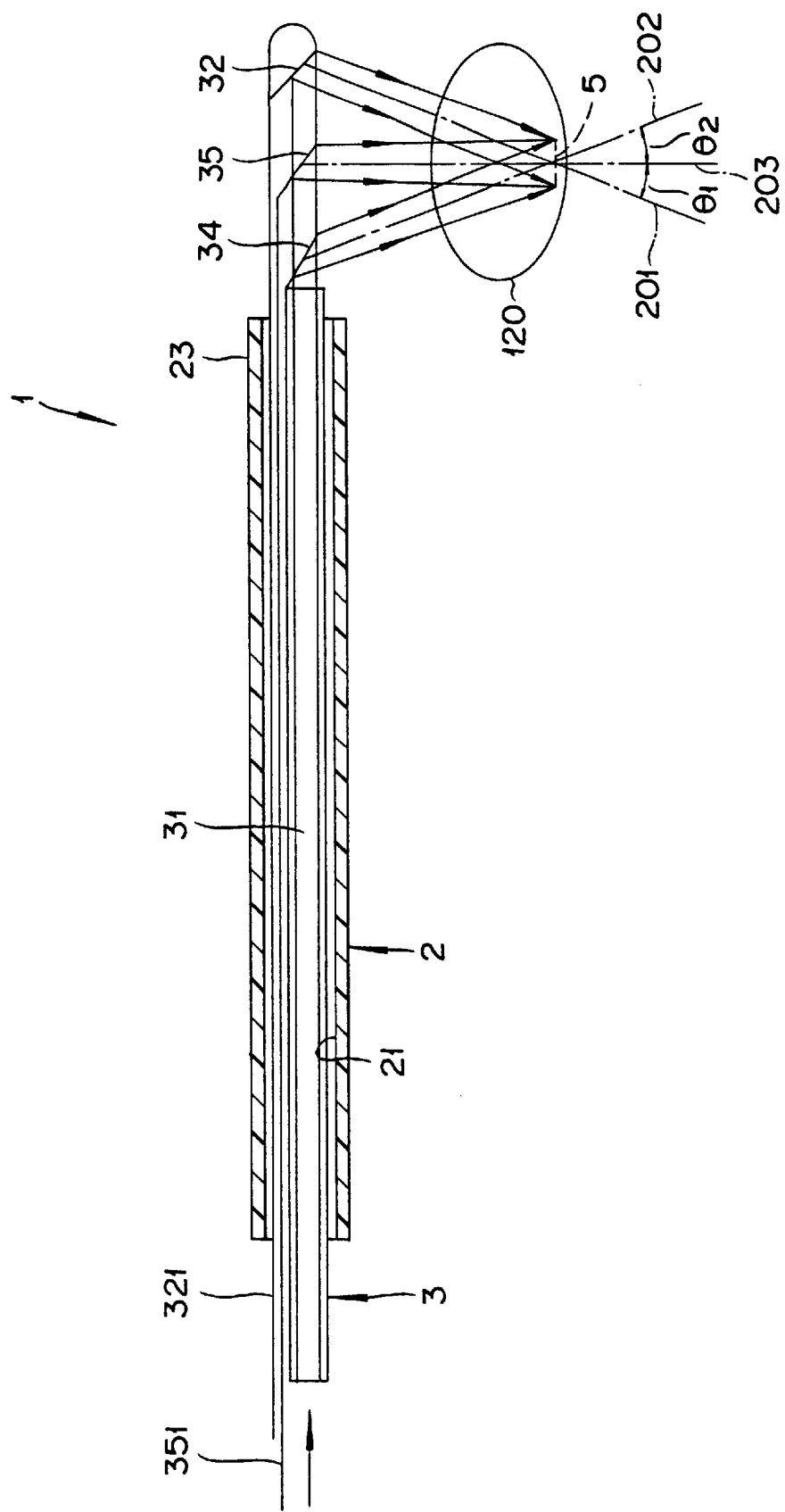
FIG. 9 is a cross section illustrating a necessary portion of a laser irradiation device according to Embodiment 3 of this invention.

FIG. 9 is a cross section illustrating Embodiment 3 of the laser irradiating device of this invention. The component parts which are shared by this Embodiment 3 and the preceding Embodiment 1 will be omitted from the following description. The main points of difference between the two embodiments in question will be described below.

The laser irradiating device 1 illustrated in the diagram comprises the sheath 2 of an elongate shape, the single laser probe 3 disposed in the working lumen 21 of the sheath 2 movably in the longitudinal direction thereof and provided with a beam splitter (emission part) 34 disposed in a fixed state at the distal end part of the optical fiber 31, the reflecting mirror (emitting part) 32, a beam splitter (emitting part) 35, and rodlike guide members 321 and 351 (means for altering the direction of emission) disposed in the working lumen 21 of the sheath 2 movably in the longitudinal direction of the sheath 2.

The reflecting mirror 32 mentioned above is installed in a fixed state at the distal end part of the guide member 321. In other words, the reflecting mirror 32 and the guide member 321 are adapted to be moved integrally in the longitudinal direction of the sheath 2.

The beam splitter 35 is installed in a fixed state at the distal end part of the guide member 351. The beam splitter 35 and the guide member 351, therefore, are enabled to produce an integrated motion in the longitudinal direction of the sheath 2.

The beam splitters 34, 35 and the reflecting mirror 32 are so disposed that they protrude in respectively fixed amounts from the distal end side of the sheath 2 and assume positions on one and the same longitudinal axis. The reflecting mirror 32 is positioned on the distal end side of the beam splitter 35 and the beam splitter 35 is positioned on the distal end side of the beam splitter 34.

The various conditions such as angle of the reflecting mirror 32 are so set as to fulfill the conditions which will be specifically described afterward and enable the laser beams reflected by the reflecting mirror 32 to be emitted in a direction inclined from the lower side in the bearings of the diagram toward the proximal end side.

The various conditions such as angle of the beam splitter 35 are so set as to fulfill the conditions which will be specifically described afterward and enable the laser beams reflected by the beam splitter 35 to be emitted toward the lower side in the bearings of the diagram, namely in the direction perpendicular to the longitudinal axis of the sheath 2.

The various conditions such as angle of the beam splitter 34 are so set as to fulfill the conditions which will be specifically described afterward and enable the laser beams reflected by the beam splitter 34 to be emitted in a direction inclined from the lower side to the distal end side in the bearings of the diagram.

The various conditions such as angle of the reflecting mirror 32 and the beam splitters 34 and 35 are so set that when the laser irradiating device 1 is viewed from the right side in the bearings of the diagram, an optical axis 201 of the laser beam reflected by the reflecting mirror 32, an optical axis 202 of the laser beam reflected by the beam splitter 34, and an optical axis 203 of the laser beam reflected by the beam splitter 35 may coincide with one another and, when the laser irradiating device 1 is viewed from the lateral side, the angle $\theta 1$ formed by the optical axes 201, 203 and the angle $\theta 2$ formed by the optical axes 202, 203 may equal each other.

When the interval between the beam splitters 34 and 35 and the interval between the beam splitter 35 and the reflecting mirror 32 are equalized with each other as illustrated in the diagram, the laser beam reflected by the reflecting mirror 32, the laser beam reflected by the splitting face (with arbitrary reflectivity) of the beam splitter 35, and the laser beam reflected by the splitting face (with arbitrary reflectivity) of the beam splitter 34 are converged at the target position 5.

The beam splitters 34, 35 are means for splitting a laser beam and their degrees of reflectivity do not need to submit to any particular restriction. The degree of reflectivity, however, is preferred to be set at ⅓ for the beam splitter 34 and ½ for the beam splitter 35. Consequently, the laser beam reflected by the reflecting mirror 32, the laser beam reflected by the splitting face of the beam splitter 35, and the laser beam reflected by the splitting face of the beam splitter 34 are equalized in quantity of light (intensity), with the result that the temperature of the surface layer part will be lowered and the safety of the device for the patient will be exalted.

Now, the operation of the Embodiment 3 will be described below.

The laser irradiating device 1 is set at a prescribed site in the body cavity and then adjusted by the use of the means for altering the direction of emission so as to make the target position 5 assume a necessary position in the target part 120. In this case, the interval between the beam splitter 34 and the beam splitter 35 and the interval between the beam splitter 35 and the reflecting mirror 32 are equalized with each other.

When the laser irradiating device 1 is then actuated to start injection of the laser beam via the proximal end part of the laser probe 3, this laser beam is guided by the optical fiber 31 from the proximal end part through the distal end part and part of the laser beam is reflected by the splitting face of the beam splitter 34 and the remainder thereof is passed through the splitting face. In other words, the laser beam is split into a reflected ray and a transmitted light.

The laser beam reflected by the splitting face of the beam splitter 34 is irradiated on the target position 5. Part of the laser beam which has passed the splitting face of the beam splitter 34 is reflected by the splitting face of the beam splitter 35 and the remainder thereof is passed through the splitting face mentioned above and split into a reflected light and a transmitted light. The laser beam reflected by the splitting face of the beam splitter 35 is irradiated on the target position 5.

The laser beam which has passed the splitting face of the beam splitter 35 is reflected by the reflecting face of the reflecting mirror 32 and irradiated on the target position 5.

Thus, the laser beam guided by the optical fiber 31 is split into a total of three laser beams by the beam splitters 34, 35 and the split laser beams are passed through different routes and converged on the target position 5. As a result, the target position 5 and the neighboring region thereof in the tissue are heated to a necessary temperature by the laser beams which impinge thereon.

Meanwhile, the site above the target part 120 (such as, for example, the part of the tissue indicated by the solid line) and the site thereunder in the bearings of the diagram are retained at a relatively low temperature because the laser beam reflected by the reflecting mirror 32, the laser beam reflected by the splitting face of the beam splitter 35, and the laser beam reflected by the splitting face of the beam splitter 34 do not overlap therein.

Then, the target position 5 is moved so as to heat the target part 120 wholly to a necessary temperature.

In the case of changing the depth of the target position 5 by moving the target position 5 in the direction perpendicular to the longitudinal axis of the sheath 2 (in the vertical direction in the bearings of the diagram), any two or all the beam splitters 34, 35 and the reflecting mirror 32 are moved in the longitudinal direction of the sheath 2 by the means for altering the direction of emission so as to alter respectively the interval between the beam splitter 34 and the beam splitter 35 and the interval between the beam splitter 35 and the reflecting mirror 32. In this case, the interval between the beam splitters 34, 35 and the interval between the beam splitter 35 and the reflecting mirror 32 are equalized with each other.

Incidentally, the movement of the beam splitter 34 in the longitudinal direction by the means for altering the direction of emission is attained by moving the laser probe 3 along the working lumen 21, the movement of the beam splitter 35 in the longitudinal direction is attained by moving the guide member 351 along e working lumen 21, and the movement of the reflecting mirror 32 in the longitudinal direction is attained by moving the guide member 321 along the working lumen 21.

While the present Embodiment 3 brings the same effect as the Embodiment 1 cited above, the Embodiment 3 particularly produces the effect of decreasing the thickness of the inserting part of the sheath 2 because it uses the single laser probe 3, namely the single optical fiber 31, splits the laser beam introduced therein into a plurality of laser beams, and emits the split laser beams. As a result, this embodiment imparts an improved ability for insertion to the laser irradiating device 1, alleviates pains and abrasions inflicted during the insertion and the extraction of the laser irradiating device 1, and reduces the burden on the patient.

In this invention, the angle $\theta_1$ formed between the optical axes 201, 203 and the angle $\theta_2$ formed between the optical axes 202, 203 may be different. It is, nevertheless, preferable to equalize $\theta_1$ and $\theta_2$. When $\theta_1$ and $\theta_2$ are equalized, the adjustment of the positions of the beam splitters 34, 35 and the reflecting mirror 32 during the adjustment and the movement of the target position 5 is facilitated because the laser beam reflected by the reflecting mirror 32, the laser beam reflected by the splitting face of the beam splitter 35, and the laser beam reflected by the splitting face of the beam splitter 34 are converged at the target position 5 when the interval between the beam splitters 34, 35 and the interval between the beam splitter 35 and the reflecting mirror 32 are equalized.

<<Embodiment 4>>

Figure 10:
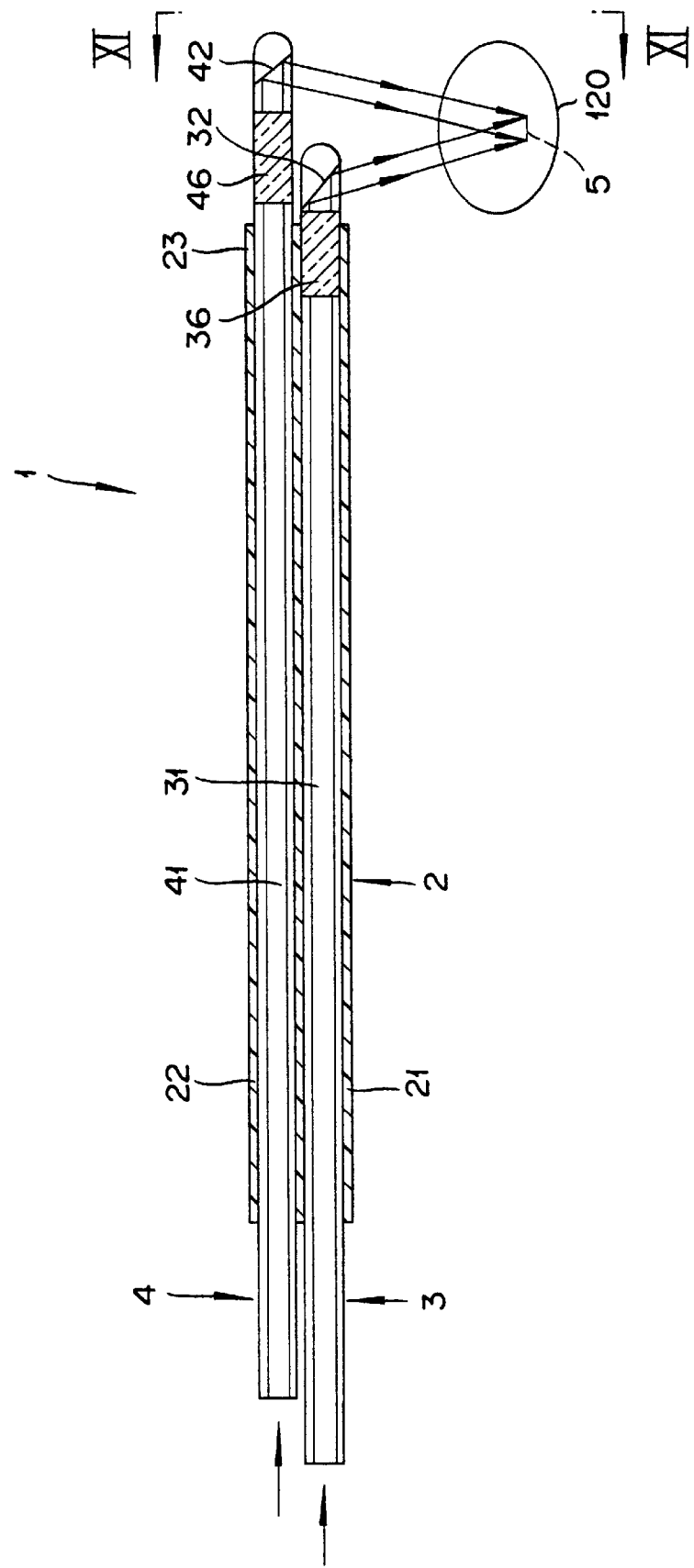
FIG. 10 is a cross section illustrating a necessary portion of a laser irradiation device according to Embodiment 4 of this invention.
Figure 11:
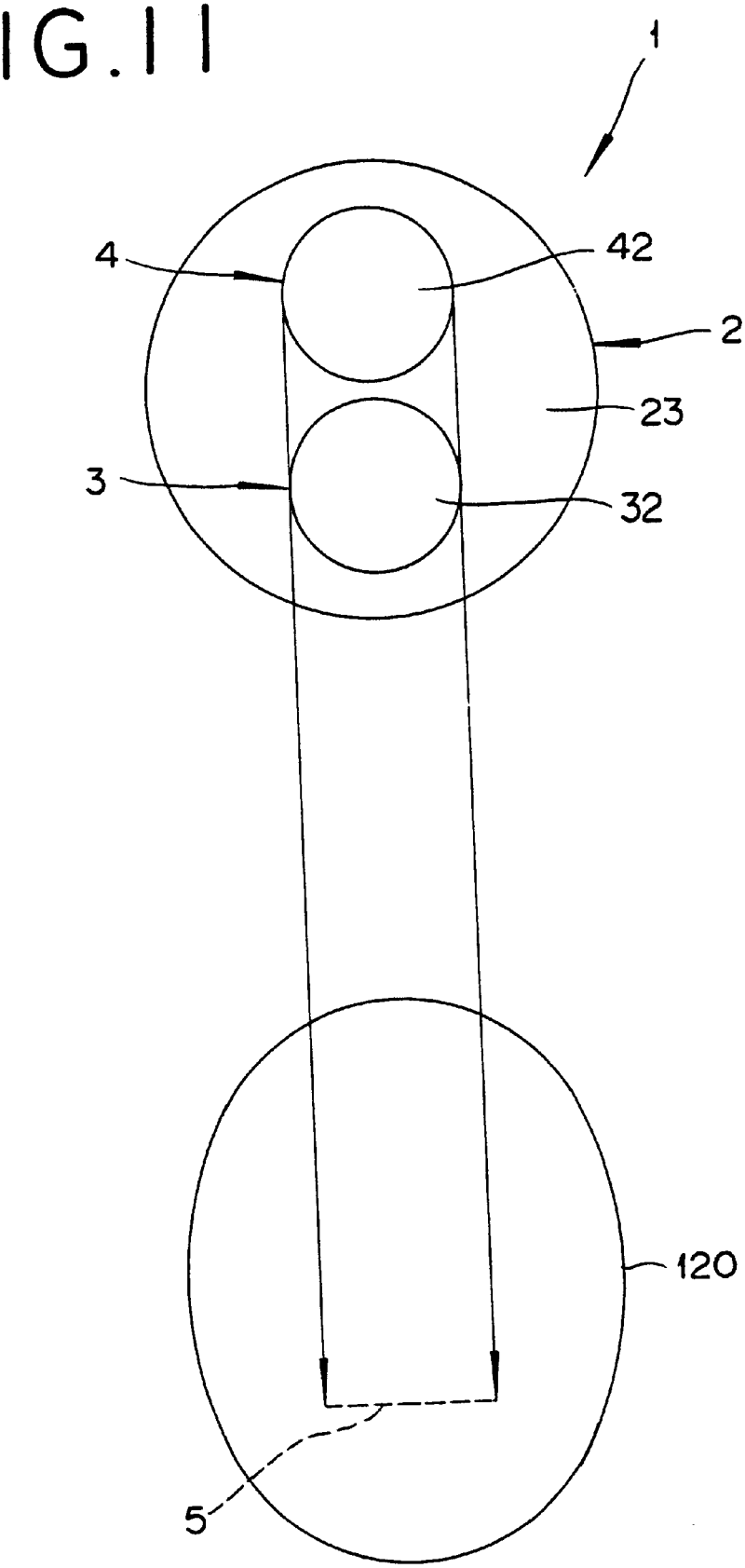
FIG. 11 is a schematic cross section taken through FIG. 10 along the line XI—XI.

FIG. 10 is a cross section illustrating the Embodiment 4 of the laser irradiating device of this invention and FIG. 11 is a schematic sectional diagram taken through FIG. 10 along the line XI—XI. The component parts which are shared by this Embodiment 4 and the preceding Embodiment 1 will be omitted from the following description. The main points of difference between the two embodiments in question will be described below.

The laser irradiating device 1 illustrated in the diagrams is provided between the distal end parts of the optical fibers 31, 41 and the corresponding reflecting mirrors 32, 42 respectively with collimating lenses 36, 46.

In consequence of this arrangement, the laser beam entering the laser probe 3 via the proximal end part thereof is guided by the optical fiber 31 from the proximal end part through the distal end part, transformed by the collimating lens 36 into a collimated ray, reflected by the reflecting mirror 32, and made to impinge on the target position 5.

Similarly, the laser beam introduced into the laser probe 4 via the proximal end part thereof is guided by the optical fiber 41 from the proximal end part through the distal end part, transformed by the collimating lens 46 into a collimated ray, reflected by the reflecting mirror 42, and made to impinge on the target position 5.

That is to say, the collimated laser beams reflected by the reflecting mirror 32 and the collimated laser beams reflected by the reflecting mirror 42 are passed through different routes and converted on the target position 5.

While the present Embodiment 4 brings the same effect as the Embodiment 1 cited above, this Embodiment 4 particularly uses collimated ray for irradiation and consequently produces the effect of allowing the laser beams to be concentrated at the target position 5 and heightening the energy densities of the laser beams at the target position 5 and the neighborhood thereof as compared with the case of irradiating diffuse light. In other words, this embodiment can lower the energy densities of the laser beams impinging on the surface layer part and therefore can prevent the surface layer part from injury with enhanced infallibility as compared with the case of using diffuse ray, providing that the energy densities of the laser beams irradiated on the target position are fixed.

For this invention, the collimating lenses 36, 46 are not always required to be positioned between the distal end parts of the optical fibers 31, 41 and the corresponding reflecting mirrors 32, 42 but are only required to assume their positions halfway along the lengths of the light paths of the laser beams.

<<Embodiment 5>>

Figure 12:
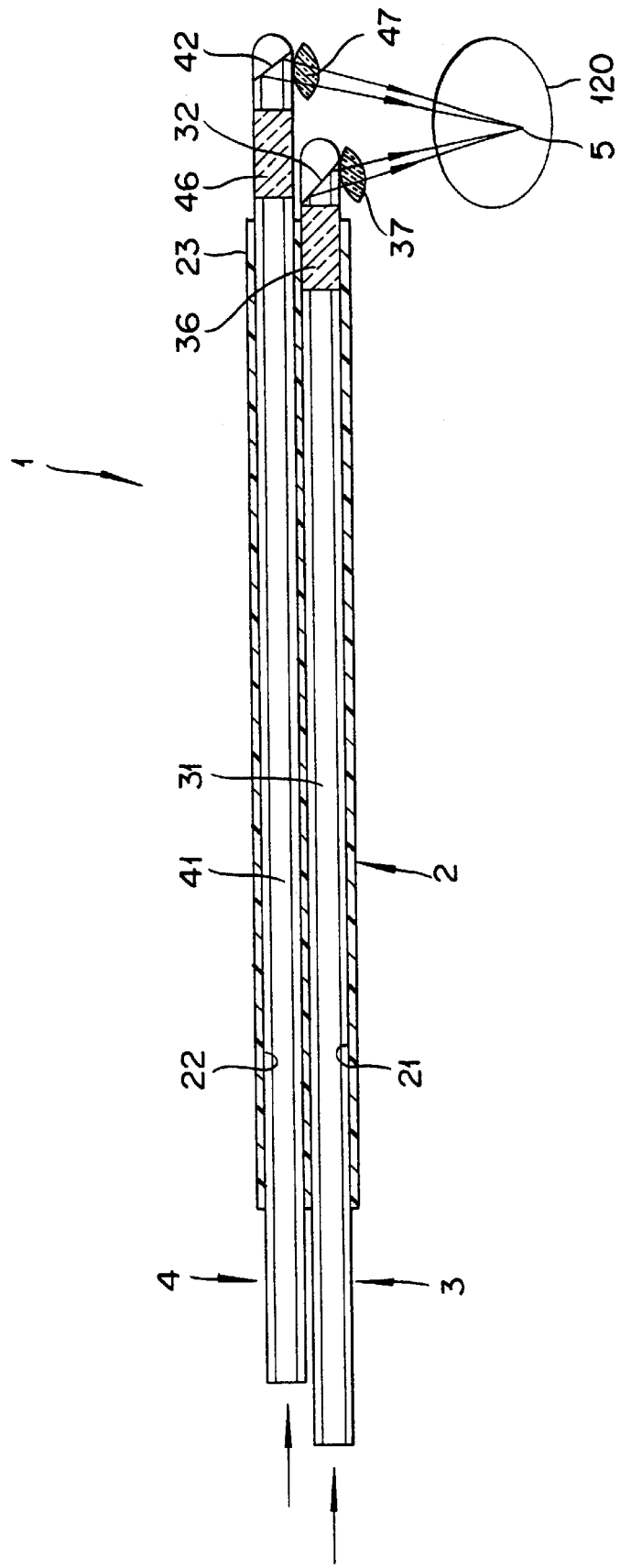
FIG. 12 is a cross section illustrating a necessary portion of a laser irradiation device according to Embodiment 5 of this invention.

FIG. 12 is a cross section illustrating a necessary portion of the Embodiment 5 of the laser irradiating device of this invention. The component parts which are shared by this Embodiment 5 and the Embodiment 1 cited above will be omitted from the following description. The main points of difference between the two embodiments in question will be described below.

The laser irradiating device 1 illustrated in the diagram is provided between distal end part of the optical fiber 31 and reflecting mirror 32 with the collimating lens 36 and on the laser beam emitting side (lower side in the bearings of the diagram) of the reflecting mirror 32 with a converging lens (condensing lens) 37.

The collimating lens 46 is installed between the distal end part of the optical fiber 41 and the reflecting mirror 42 and a converging lens (condensing lens) 47 is installed on the laser beam emitting side (the lower side in the bearings of the diagram) of the reflecting mirror 42.

In consequence of this arrangement, the laser beam introduced into the laser probe 3 via the proximal end part thereof is guided by the optical fiber 31 from the proximal end part through the distal end part, transformed into collimated rays by the collimating lens 36, reflected by the reflecting mirror 32 in the direction of the target position 5, transformed into a converging ray by the converging lens 37, and made to impinge on the target position 5.

Then, the laser beam introduced into the laser probe 4 via the proximal end part thereof is guided by the optical fiber 41 from the proximal end part through the distal end part, transformed into a collimated ray by the collimating lens 46, reflected by the reflecting face of the reflecting mirror 42 in the direction of the target position 5, transformed into a convergent ray by the converging lens 47, and made to impinge on the target position 5.

That is to say, the collimated laser beams reflected by the reflecting mirror 32 and the collimated laser beams reflected by the reflecting mirror 42 are respectively transformed into converging rays, passed through different light paths, and converged on the target position 5.

Though the present Embodiment 5 brings the same effect as the Embodiment 1 cited above, this Embodiment 5 particularly uses convergent light for irradiation and consequently produces the effect of allowing the laser beams to be concentrated at the target position 5 and heightening the energy densities of the laser beams at the target position 5 and the neighborhood thereof as compared with the case of irradiating diffuse light. This embodiment, therefore, can lower the energy densities of the laser beams impinging on the surface layer part and can prevent the surface layer part from injury with enhanced infallibility as compared with the case of using a diffuse light, providing that the energy densities of the laser beams impinging on the target position 5 are fixed.

This invention does neither confine the positions of the collimating lenses 36, 46 to the ranges between the distal end parts of the optical fibers 31, 41 and the reflecting mirrors 32, 42 nor restrict the positions of the converging lenses 37, 47 to the laser beam emitting sides of the reflecting mirrors 32, 42. The collimating lenses 36, 46 and the converging lenses 37, 47 may be respectively positioned halfway in the lengths of the light paths of the laser beams. optionally, the laser irradiating device 1 may be so constructed as to omit the collimating lenses 36, 46 and rely on the converging lenses 37, 47 to effect transformation of diffuse light into convergent light.

<<Embodiment 6>>

Figure 13:
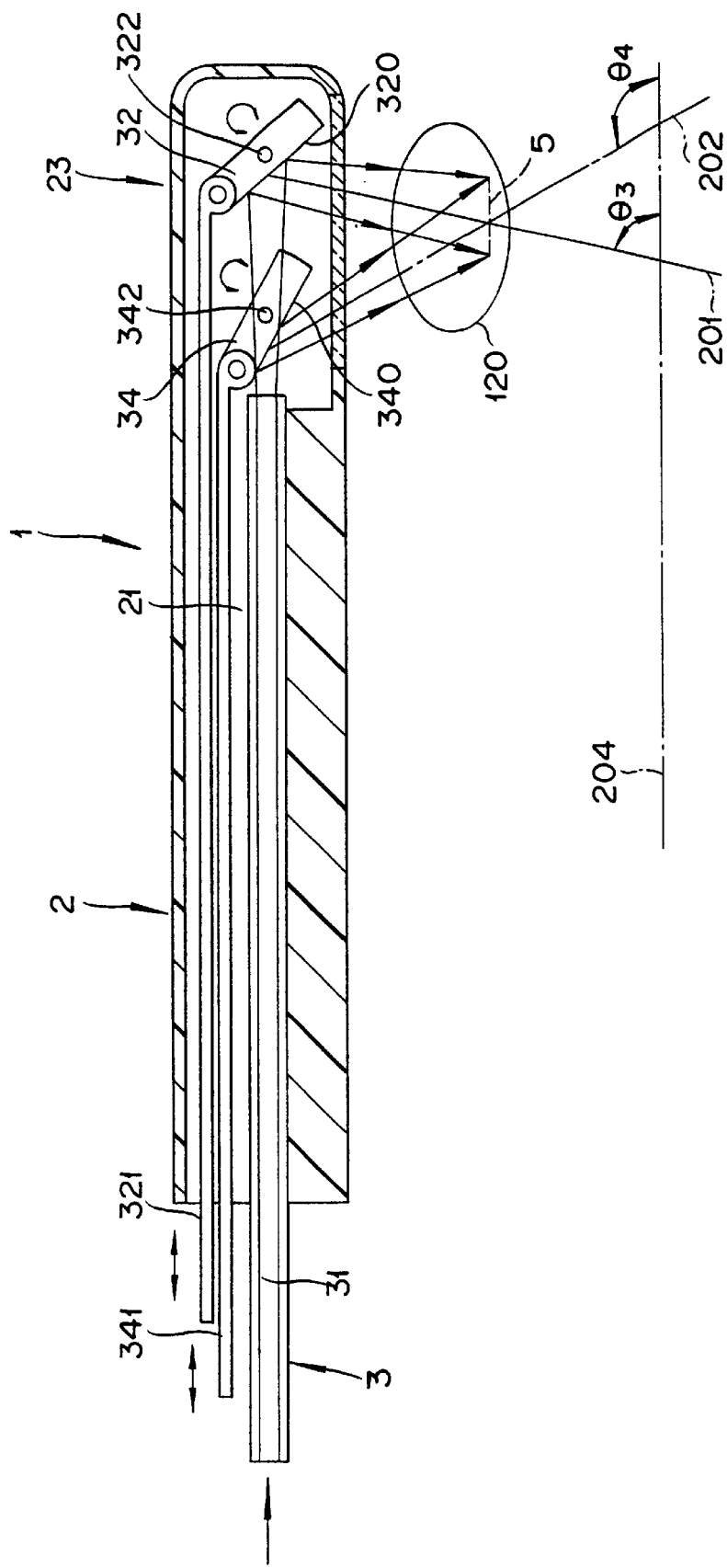
FIG. 13 is a cross section illustrating a necessary portion of a laser irradiation device according to Embodiment 6 of this invention.

FIG. 13 is a cross section illustrating a necessary portion of the Embodiment 6 of the laser irradiating device of this invention. The component parts which are shared by this Embodiment 6 and the Embodiment 3 cited above will be omitted from the following description. The main points of difference between the two embodiments in question will be described below.

The laser irradiating device 1 illustrated in the diagram is roughly a modification of the laser irradiating device 1 of the Embodiment 3 illustrated in FIG. 9 mentioned above in respect that the means for altering the direction of irradiation is adapted to rotate.

This laser irradiating device 1 is provided with the elongate sheath 2 having the working lumen 21 formed therein, the optical fiber (light guiding member) 31 installed inside the working lumen 21 of the sheath 2, the reflecting mirror (emitting part) 32, the beam splitter (emitting part) 34, and rodlike guide members 321 and 341.

The working lumen 21 is formed parallel to the longitudinal axis of the sheath 2 and is opened on the proximal end side of the sheath 2. The part on the lower side in the bearings of FIG. 13 of at least the distal end part 23 of the sheath 2 is pervious to light. In this case, a window pervious to light may be formed in the part on the lower side in the bearings of FIG. 13 of the distal end part 23 of the sheath 2 or the sheath 2 may be wholly pervious to light. Otherwise, an opening may be formed in the part on the lower side in the bearings of FIG. 13 of the distal end part 23 of the sheath 2.

The optical fiber 31 is set in place nearly at the center of the sheath 2 parallel to the longitudinal axis of the sheath 2. The proximal end part of this optical fiber 31 protrudes from the proximal end of the sheath 2 and the distal end part thereof assumes the position thereof near the distal end part of the sheath 2.

The beam splitter 34 is positioned in such a manner on the distal end side of the optical fiber 31 that the angle of inclination thereof relative to the longitudinal axis of the sheath 2 may be varied. Specifically, the beam splitter 34 is supported rotatably relative to the sheath 2 by an axis 342 and the beam splitter 34 at the end part thereof is rotatably supported on the distal end part of the guide member 341.

The guide member 341 is installed movable in the longitudinal direction of the sheath 2 (the direction parallel to the longitudinal axis of the sheath 2) and in the direction perpendicular to the longitudinal axis of the sheath 2. The proximal end part of this guide member 341 protrudes from the proximal end of the sheath 2.

The reflecting mirror 32 is positioned in such a manner on the distal end side of the beam splitter 34 that the angle of inclination thereof relative to the longitudinal axis of the sheath 2 may be varied. To be specific, the reflecting mirror 32 is supported rotatably relative to the sheath 2 by an axis 322 and the reflecting mirror 32 at the end part thereof is rotatably supported on the distal end part of the guide member 321.

The guide member 321 is set in place movably in the longitudinal direction of the sheath 2 and in the direction perpendicular to the longitudinal axis of the sheath 2. The proximal end part of the guide member 321 protrudes from the proximal end of the sheath 2.

The reflecting mirror 32 and the beam splitter 34 are positioned in the longitudinal direction of the sheath 2, namely on a straight line parallel to the longitudinal axis of the sheath 2 (the longitudinal axis of the optical fiber 31). The axis 322 for supporting the reflecting mirror 32 and the axis 34 for supporting the beam splitter 34 are disposed parallel to each other.

In consequence of this arrangement, the aforementioned means for altering the direction of emission which enables the motions of the guide members 321 and 341 to rotate the reflecting mirror 32 and the beam splitter 34 round the axis 322 or the axis 342 as the center and alter the direction of emitting the laser beams is completed.

While the laser irradiating device 1 is held in the state illustrated in FIG. 13, the laser beam emitted from the beam splitter 34, namely the laser beam reflected by the splitting face (with arbitrary reflectivity) of the beam splitter 34 is issued in the direction inclined from the lower side to the distal end side in the bearings of the diagram (inclined toward the distal end) and the laser beam emitted from the reflecting mirror 32, namely the laser beam reflected by the reflecting face 320 of the reflecting mirror 32, is issued in the direction inclined from the lower side to the proximal end side in the bearings of the diagram (inclined toward the proximal end side).

As a result, the laser beam reflected by the splitting face 340 of the beam splitter 34 and the laser beam reflected by the reflecting face 320 of the reflecting mirror 32 overlap (coincide) at the target position on the lower side in the bearings of the figure.

In the present laser irradiating device 1, the target position 5 can be moved in an arbitrary direction by manipulating the guide member 321 and the guide member 341 so as to satisfy the condition, θ3<θ4, wherein θ3 stands for the angle to be formed by the optical axis 201 of the laser beam reflected by the reflecting face 320 of the reflecting mirror 32 and a straight line 204 parallel to the longitudinal axis of the sheath 2 and θ4 for the angle to be formed by the optical axis 202 of the laser beam reflected by the splitting face 340 of the beam splitter 34 and the straight line 204, thereby altering the angles of the reflecting face 320 of the reflecting mirror 32 and the splitting face 340 of the beam splitter 34, namely the directions of emission of the laser beams (the direction of irradiation). The performance of the laser irradiating device 1 in this respect will be described more specifically herein below.

Though the beam splitter 34 does not need to impose any particular restriction on the degree of reflectivity (the degree of refractivity of the splitting face 340), this degree of reflectivity is preferred to be set at ½.

By setting the degree of reflectivity of the beam splitter 34 at ½, the laser beam reflected by the reflecting face 320 of the reflecting mirror 32 and the laser beam reflected by the splitting face 340 of the beam splitter 34 are equalized in quantity of light. As a result, the safety of the laser irradiating device 1 for the patient is high because the temperature of the surface layer part 101 of the tissue 100 can be further lowered.

Now, the operation of this Embodiment 6 will be described below.

For a start, the sheath 2 is inserted into the body cavity 110 and then, with the distal end part 23 thereof taken as a prescribed position, set therein in such a manner that the target position (light converging position) 5 may assume a necessary position in the target part 120 for irradiation.

In the case of adjusting the target position 5 in the direction perpendicular to the longitudinal axis of the sheath 2 (in the vertical direction in the bearings of the diagram) by the use of the means for altering the direction of emission, either or both of the reflecting mirror 32 and the beam splitter 34 are rotated in necessary directions the consequently adjusting the directions of emission of the laser beams, namely either or both of the θ3 and the θ4.

In this case, when the θ3 is enlarged or the θ4 is reduced, the target position 5 moves in the direction of departing from the sheath 2 (the lower side in the bearings of FIG. 13).

Conversely, when the θ3 is reduced or the θ4 is enlarged, the target position 5 moves in the direction of approximating closely to the sheath 2 (the upper side in the bearings of the diagram).

Further, for the purpose of adjusting the target position 5 in the longitudinal direction of the sheath 2, the directions of emission of the laser beams, namely the angles θ3 and θ4, are adjusted by either moving the laser irradiating device 1 wholly in a prescribed direction (the longitudinal direction of the sheath 2) or rotating the reflecting mirror 32 and the beam splitter 34 in respectively prescribed directions.

When the adjustment of the target position 5 in the longitudinal direction of the sheath 2 is implemented by rotating the reflecting mirror 32 and the beam splitter 34, the burden on the patient can be alleviated and the operation of the laser irradiating device 1 can be facilitated because the sheath 2 is no longer required to be moved.

The target position 5 is adjusted in the circumferential direction of the sheath 2 by rotating the laser irradiating device 1 wholly clockwise or counterclockwise in the bearings of FIG. 2.

The adjustment of the target position 5 in the direction perpendicular to the longitudinal axis of the sheath 2, that in the longitudinal direction of the sheath 2, and that in the circumferential direction of the sheath 2 may be respectively carried out as occasion demands.

Then, when the laser beam generating device (not shown) is actuated to start injection of a laser beam into the optical fiber 31 via the proximal end part thereof, the laser beam which has entered the optical fiber 31 via the proximal end part is guided by the optical fiber 31 from the proximal end part through the distal end part, with the result that part of the laser beam is reflected by the splitting face 340 of the beam splitter 34 and the remainder thereof is passed through the splitting face 340 (in consequence of the division into the reflected ray and the transmitted ray). The laser beam which has been reflected by the splitting face 340 of the beam splitter 34 is made to impinge on the target position 5.

The laser beam which has passed the splitting face 340 of the beam splitter 34 is reflected by the reflecting face 320 of the reflecting mirror 32 and the reflected light is made to impinge on the target position 5.

To be specific, the laser beam which has been guided by the optical fiber 31 is divided into two parts by the beam splitter 34 and the divided laser beams (the laser beam reflected by the reflecting face 320 of the reflecting mirror 32 and the laser beam reflected by the splitting face 340 of the beam splitter 34) are passed through different routes and converged (condensed) on the target position 5 on the lower side in the bearings of FIG. 13.

The target position 5 and the neighboring site (region) thereof in the tissue 100 are heated to a necessary temperature by the laser beam which impinges thereon.

Meanwhile, the cite on the upper side (such as, for example, the surface layer part of the tissue 100) and the cite on the lower side of the target part 120 in the bearings of the diagram are retained respectively at relative low temperatures because the laser beam reflected by the reflecting mirror 32 and the laser beam reflected by the beam splitter 34 do not overlap.

Then, the target part 120 for irradiation is wholly heated to a necessary temperature by moving the target position 5 (by continuously moving the target position 5) by the use of the means for altering the direction of emission.

In the case of moving the object position 5 in the direction perpendicular to the longitudinal axis of the sheath 2 (in the vertical direction in the bearings of the diagram), the directions of emission of laser beams, namely either or both of the angles θ3 and θ4, are varied by rotating either or both of the reflecting mirror 32 and the beam splitter 34 in prescribed directions as described above.

Figure 14:
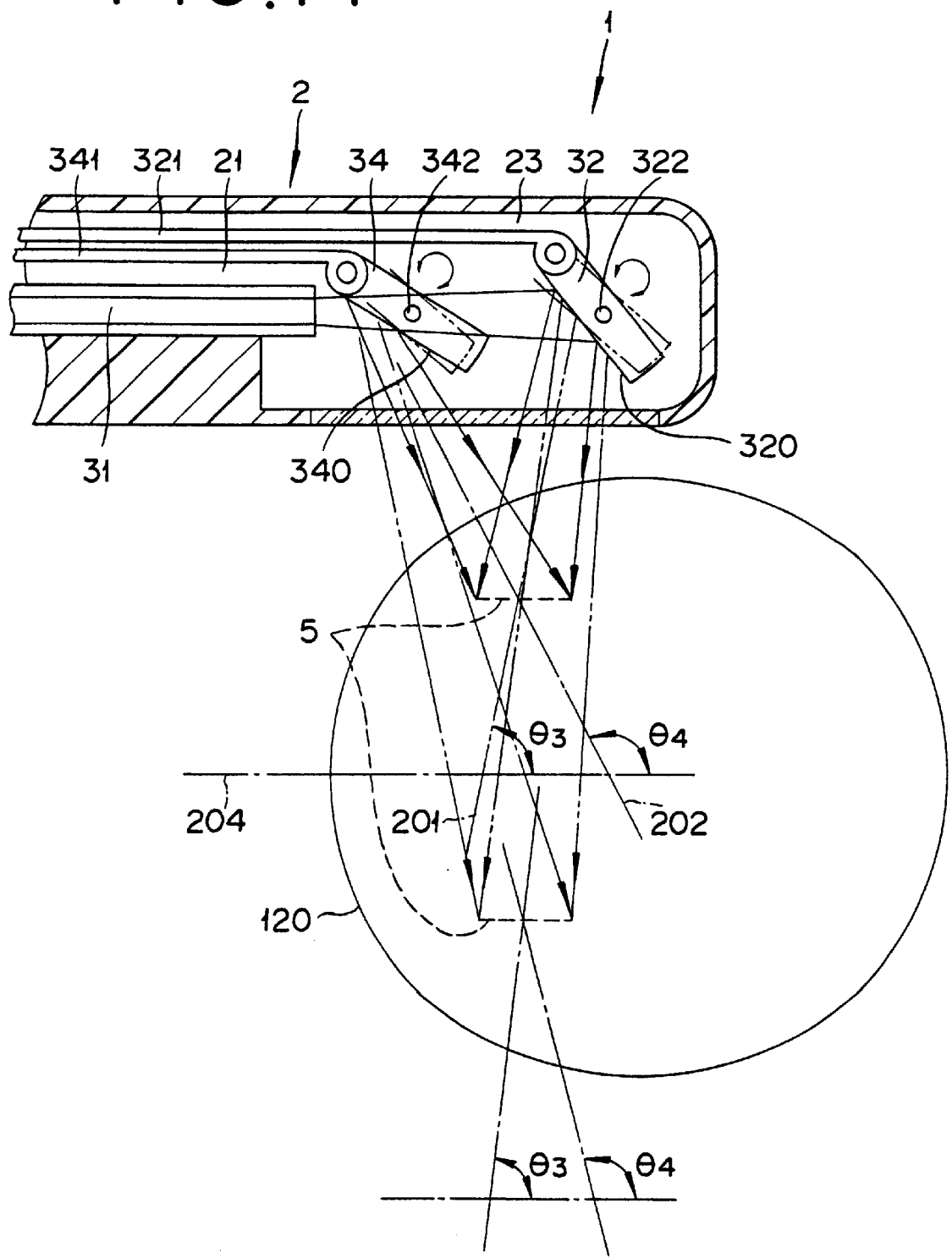
FIG. 14 is a cross section illustrating a necessary portion of the case of vertically moving the target position of the laser irradiation device.

When the guide member 321 of the means for altering the direction of emission in the state illustrated in FIG. 14 is moved to the left side in the bearings of FIG. 14, for example, the reflecting mirror 32 rotates counterclockwise and assume the state indicated by a two-dot chain line, with the result that the direction of emission of the laser beam from the reflecting mirror 32, namely the angle of the optical axis 201 of the laser beam reflected by the reflecting face 320 of the reflecting mirror 32 relative to the longitudinal axis of the sheath 2, will be altered. In this case, the angle θ3 which is formed between the optical axis 201 of the laser beam and the straight line 204 parallel to the longitudinal axis of the sheath 2 is enlarged.

Then, when the guide member 341 is moved to the right side in the bearings of FIG. 14, the beam splitter 34 rotates clockwise in the bearings of FIG. 14 and assumes the state indicated by a two-dot chain line, with the result that the direction of emission of the laser beam from the beam splitter 34, namely the angle which is formed between the optical axis 202 of the laser beam reflected by the splitting face 340 of the beam splitter 34 and the longitudinal axis of the sheath 2, will be varied. In this case, the angle θ4 which is formed between the optical axis 202 of the laser beam and the straight line 204 is decreased.

As a result, the target position 5 will be moved to the lower side in the bearings of FIG. 14.

Conversely, in the case of moving the target position 5 to the upper side in the bearings of the diagram, the guide member 321 is moved to the right side, the reflecting mirror 32 is rotated clockwise, the guide member 341 is moved to the left side, and the beam splitter 34 is rotated counterclockwise.

As a result, the angle θ3 is reduced and the angle θ4 is enlarged and the target position 5 is moved to the upper side.

In the case of moving the target position 5 in the direction perpendicular to the longitudinal axis of the sheath 2, the target position 5 can be moved exclusively in the direction perpendicular to the longitudinal axis of the sheath 2 without being moved in the longitudinal direction of the sheath by setting either of the angles θ3 and θ4 at 90° and altering the other angle (by setting the direction of emission of either of the laser beam from the reflecting mirror 32 and the laser beam from the beam splitter 34 in the lateral direction and altering the direction of emission of the remaining laser beam).

Then, in the case of moving the target position 5 in the longitudinal direction of the sheath 2, the directions of emission of the laser beams, namely the angles θ3 and θ4, are respectively altered by moving the laser irradiation device 1 wholly in a prescribed direction (the longitudinal direction of the sheath 2) or rotating the reflecting mirror 32 and the beam splitter 34 in respectively prescribed directions as described above. For the same reason as given above, the target position 5 is preferred to be moved in the longitudinal direction of the sheath 2 by rotating the reflecting mirror 32 and the beam splitter 34.

When the guide member 321 held in the state illustrated in FIG. 14 is moved to the left side in the bearings of FIG. 14, for example, the reflecting mirror 32 is rotated counterclockwise, with the result that the direction of emission of the laser beam from the reflecting mirror 32, namely, the angle formed between the optical axis 201 of the laser beam reflected by the reflecting face of the reflecting mirror 32 and the longitudinal axis of the sheath 2, will be altered. In this case, the angle θ3 which is formed between the optical axis 201 of the laser beam and the straight line 204 is enlarged as illustrated in FIG. 15.

By the same token, when the guide member 341 is moved to the left side in the bearings of FIG. 14, the beam splitter 34 is rotated counterclockwise, with the result that the direction of emission of the laser beam from the beam splitter 34, namely the angle to be formed between the optical axis 202 of the laser beam reflected by the splitting face 340 of the beam splitter 34 and the longitudinal axis of the sheath 2, will be altered. In this case, the angle θ4 to be formed between the optical axis 202 of the laser beam and the straight line 204 is enlarged as illustrated in FIG. 15.

Figure 15:
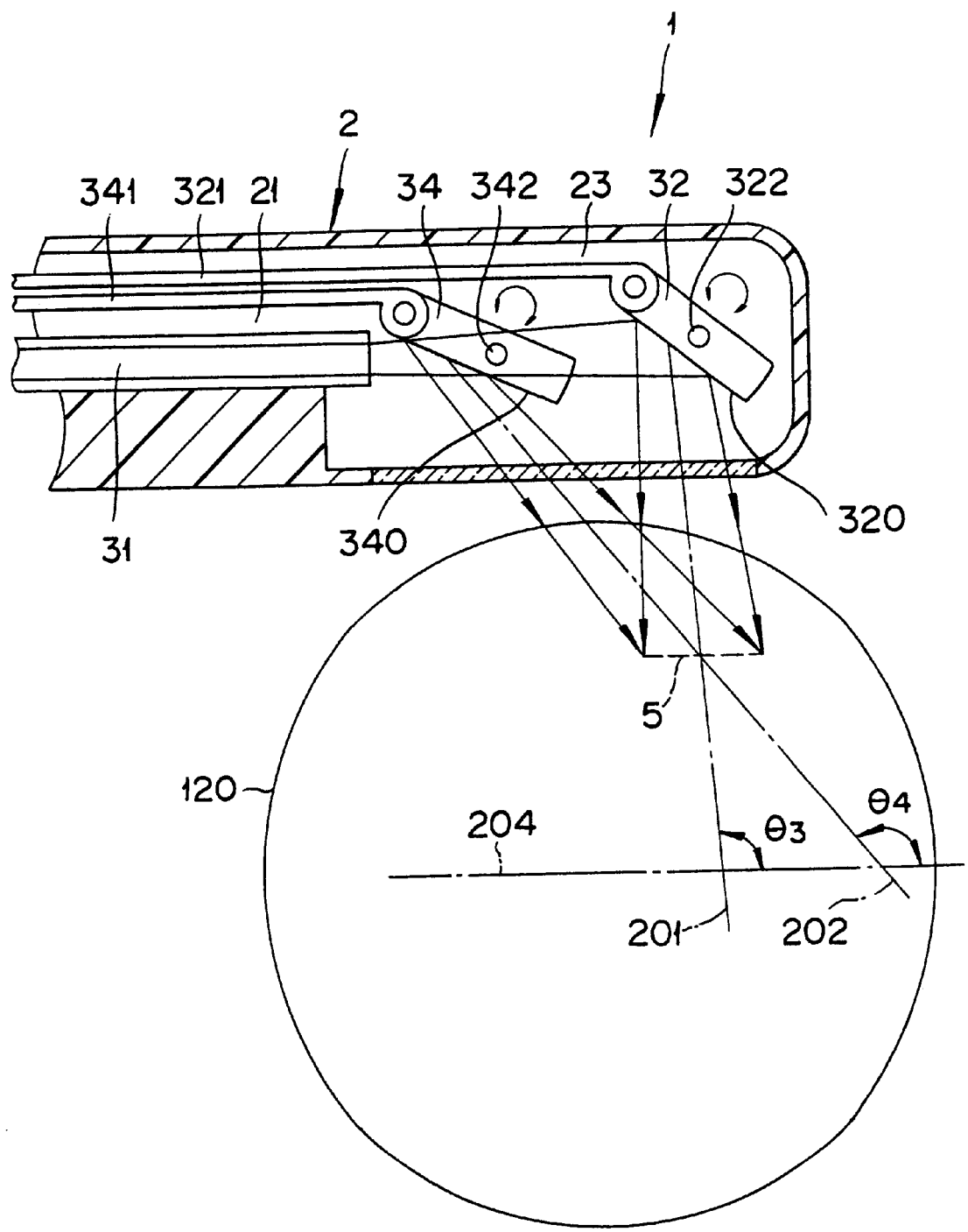
FIG. 15 is a cross section illustrating a necessary portion of the case of laterally moving the target position of the laser irradiation device.

As a result, the target position 5 moves to the right side in the bearings of FIG. 14 and assumes the state illustrated in FIG. 15.

Conversely, in the case of moving the target position 5 to the left side in the bearings of FIG. 15, the reflecting mirror 32 and the beam splitter 34 are respectively rotated clockwise in the bearings of FIG. 15 by moving the guide members 321 and 341 respectively to the right side in the bearings of FIG. 15.

As a result, the angles θ3 and θ4 are respectively reduced and the target position 5 is moved to the left side in the bearings of FIG. 15.

Then, the target position 5 is moved in the circumferential direction of the sheath 2 by rotating the laser irradiating device 1 wholly either clockwise or counterclockwise as described above.

Though the present Embodiment 6 brings the same effect as the embodiment mentioned above, this Embodiment 6 particularly produces the effect of enabling the target position 5 to be moved in an arbitrary direction by the use of the means for altering the direction of emission, especially the effect of enabling the target position 5 to be moved in the direction perpendicular to the longitudinal axis of the sheath 2. According to this embodiment, therefore, the target part 120 for irradiation held at an arbitrary position or the target part 120 for irradiation having an arbitrary shape and an arbitrary size can be wholly heated uniformly to a necessary temperature easily and infallibly (can be prevented from being locally heated excessively or insufficiently).

Further, since the laser irradiating device 1 is capable of moving the target position 5 in the direction perpendicular to the longitudinal axis of the sheath 2 by rotating either or both of the reflecting mirror 32 and the bean splitter 34, this laser irradiating device 1 does not need to be exchanged for the sake of altering the depth of the target position 5. As a result, the operation can be facilitated and the burden on the patient can be alleviated.

The laser irradiating device 1 is capable of moving the target position 5 in the longitudinal direction of the sheath 2 without moving the sheath 2 by rotating the reflecting mirror 32 and the beam splitter 34. Even when the inserting part of the laser irradiating device 1 can be driven only halfway along the whole of a necessary depth as by reason of a relatively narrow opening of the body cavity 110, the target part 120 can be heated to the necessary temperature by irradiating the target part 120 with the laser beam.

Figure 16:
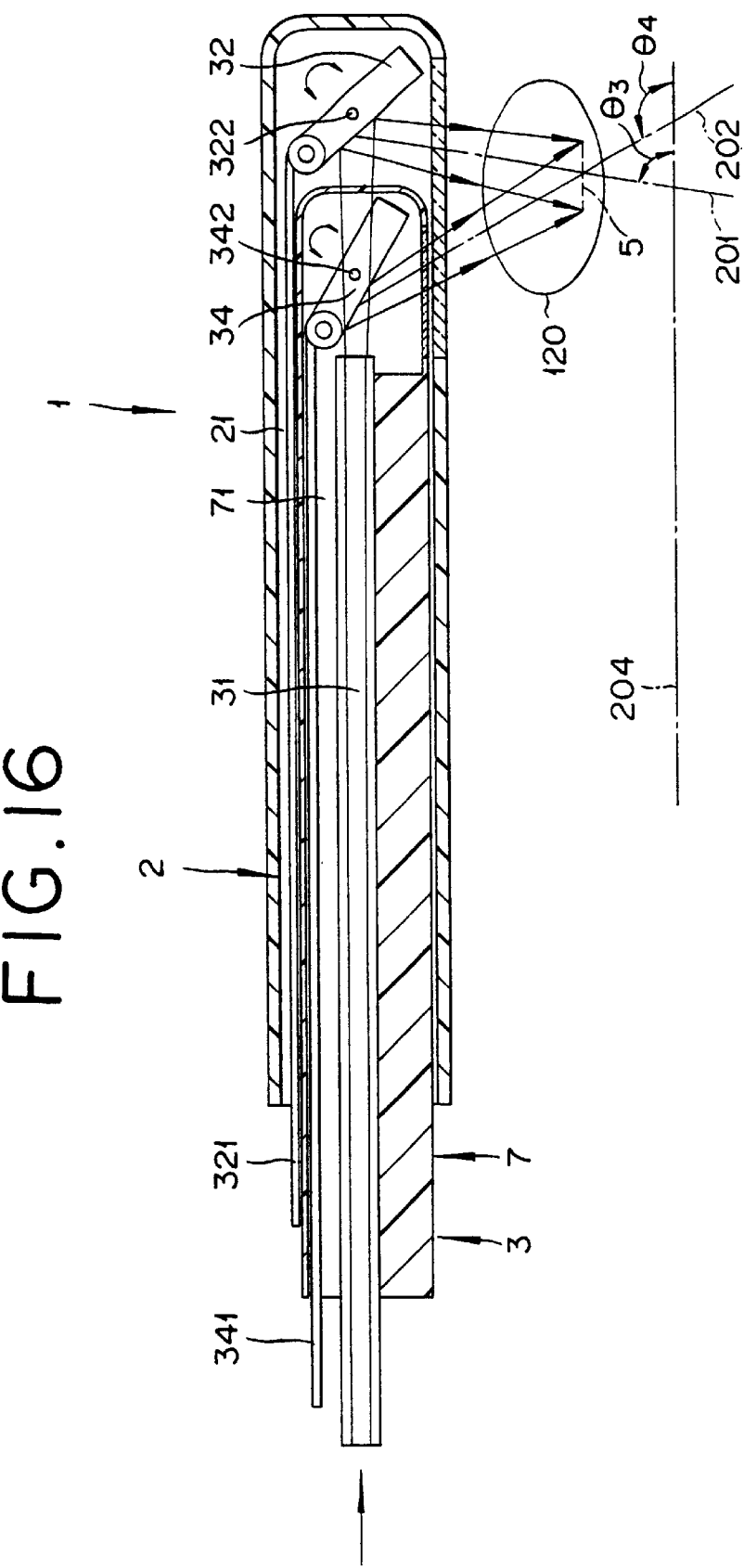
FIG. 16 is a cross section illustrating a necessary portion of a typical modification of Embodiment 6 mentioned above.

FIG. 16 is a cross section illustrating a necessary portion of a typical modification of the preceding Embodiment 6. The component parts which are shared by this modification and the Embodiment 6 cited above will be omitted from the following description. The main points of difference between the two embodiments in question will be described below.

The laser irradiating device 1 illustrated in the diagram is provided with the elongate sheath 2 having the working lumen 21 formed therein, the single laser probe 3 installed in the working lumen 21, the reflecting mirror 32, and the rodlike guide member 321.

The laser probe 3 is composed of an elongate sheath 7 having a working lumen 71 formed therein, an optical fiber 31 installed in the working lumen 71, the beam splitter 34, and the rodlike guide member 341. The working lumen 71 opens respectively into the distal end and the proximal end of the sheath 7.

The optical fiber 31 is disposed nearly at the center of the sheath 7 parallel to the longitudinal axis of the sheath 7.

Though this arrangement allows the present modification to bring the same effect as the Embodiment 6 mentioned above, this modification particularly in the case of moving the target position 5 in the direction perpendicular to the longitudinal axis of the sheath (in the vertical direction in the bearings of the diagram), namely in the case of altering the depth of the target position 5, produces the effect of facilitating the operation and alleviating the burden on the patient because it effects the alteration of the interval between the beam splitter 34 and the reflecting mirror 32 by moving the laser probe 3 in the longitudinal direction of the sheath 2.

<<Embodiment 7>>

Figure 17:
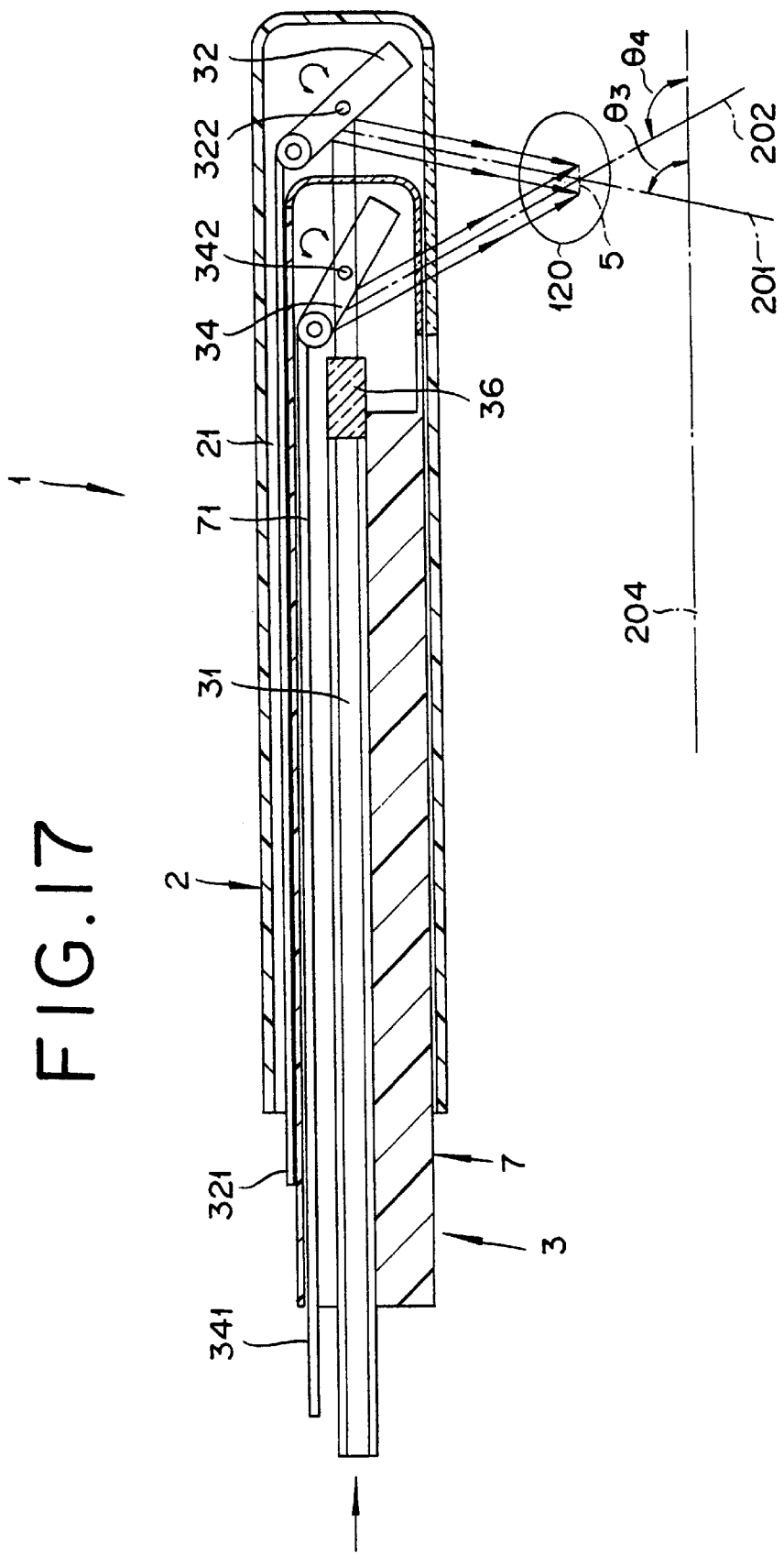
FIG. 17 is a cross section illustrating a necessary portion of a laser irradiation device according to Embodiment 7 of this invention.

FIG. 17 is a cross section illustrating a necessary portion of the Embodiment 7 of the laser irradiating device of this invention. The component parts which are shared by this Embodiment 7 and the Embodiment 6 cited above and the modification thereof will be omitted from the following description. The main points of difference between the two embodiments in question will be described below.

The laser irradiating device 1 illustrated in the diagram has a collimating lens 36 installed at the distal end part of the optical fiber 31, namely between the distal end part of the optical fiber 31 and the beam splitter 34.

Inconsequence of this arrangement, the laser beam which has been injected into the laser probe 3 via the proximal end part thereof is guided by the optical fiber 31 from the proximal end part through the distal end part and transformed by the collimating lens 36 into a collimated ray. Part of the collimated lay is reflected by the splitting face of the beam splitter 34 and the remainder thereof is passed through the splitting face and divided into a reflected light and a transmitted light. The laser beam reflected by the splitting face of the beam splitter 34 is made to impinge on the target position 5. The laser beam which has passed the splitting face of the beam splitter 34 is reflected by the reflecting mirror 32 and made to impinge on the target position 5.

As a result, the laser beam which has been guided by the optical fiber 31 is transformed by the collimating lens 36 into a collimated ray and then split into two rays by the beam splitter 34. The split laser beams are passed through different routes and converged at the target position 5.

Though the present Embodiment 7 brings the same effect as the Embodiment 6 cited above, this Embodiment 7 particularly uses a collimated ray for irradiation and consequently produces the effect of enabling the laser beams to be converged at the target position 5 and exalting the energy densities of the laser beams at the target position 5 and in the neighborhood thereof as compared with the case of using a diffuse ray for irradiation. In other words, this embodiment can lower the energy densities of the laser beams which impinge on the surface layer part and prevent the surface layer part from injury infallibly as compared with the case of using diffuse ray for irradiation, providing that the energy densities of the laser beams impinging on the target position 5 are fixed.

Incidentally, for this invention, the position of the collimating lens 36 is only required to fall halfway in the entire length of the light path of the laser beam and does not need to be confined between the distal end part of the optical fiber 31 and the reflecting mirror 32.

<<Embodiment 8>>

Figure 18:
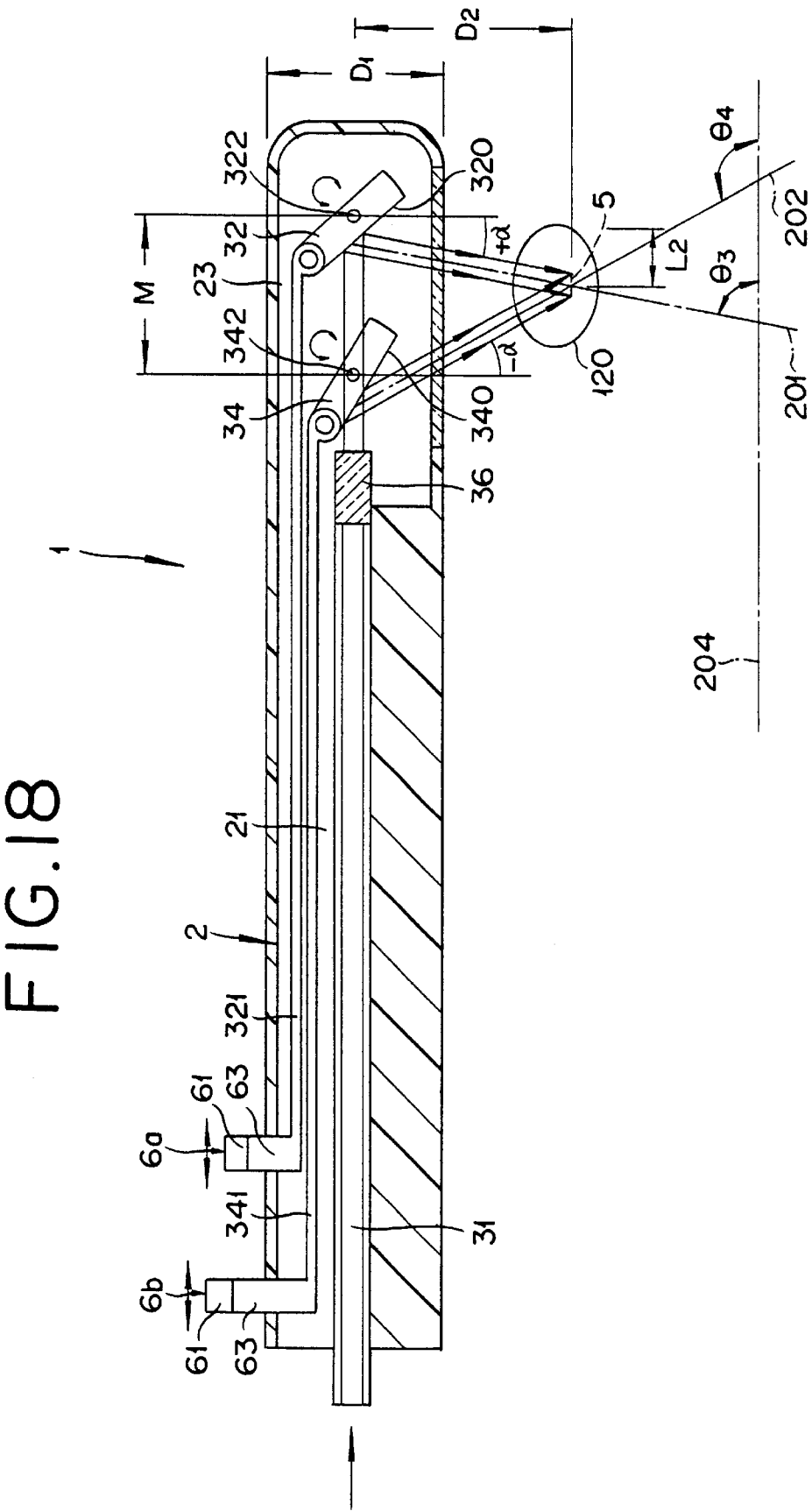
FIG. 18 is a cross section illustrating a necessary portion of a laser irradiation device according to Embodiment 8 of this invention.
Figure 19:
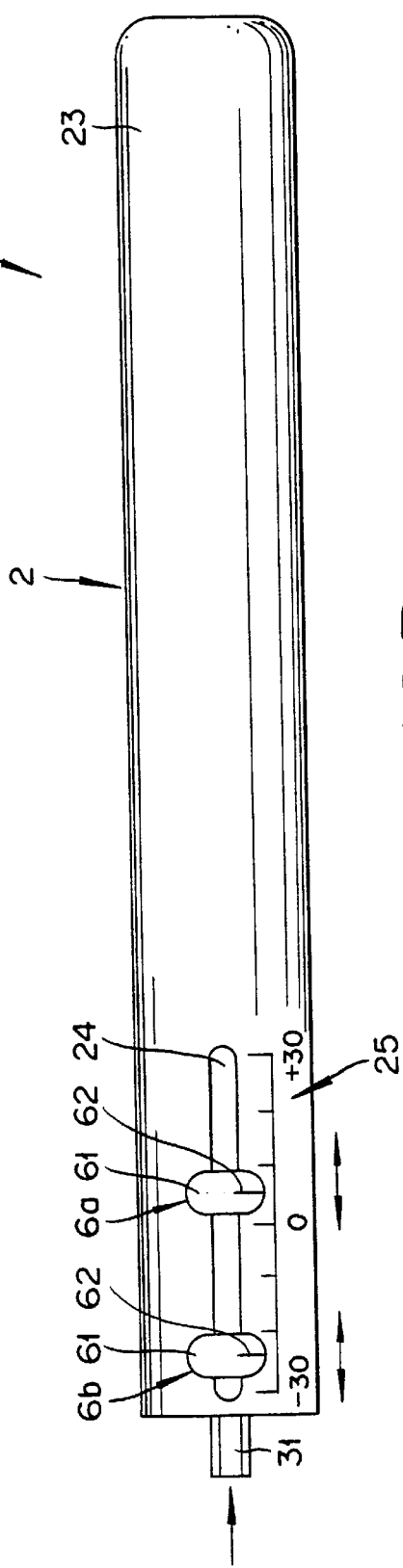
FIG. 19A is a side view of Embodiment 18.
FIG. 19B is a table showing the relation between the lever position on the one hand and the depth of irradiation and the position of irradiation on the other hand.

FIG. 18 is a cross section illustrating a necessary portion of the Embodiment 8 of the laser irradiating device of this invention, FIG. 19A is a side view of FIG. 18, and FIG. 19B is a table showing the relation between the lever position on the one part and the depth of irradiation and the position of irradiation on the other hand. The component parts which are shared by this Embodiment 8 and the embodiments cited above will be omitted from the following description. The main points of difference between the two embodiments in question will be described below.

As illustrated in the diagrams, this laser irradiating device 1 is provided with the guide members 321, 341 as means for altering the direction of emission. These guide members 321, 341 are provided respectively with levers (manipulating members) 6a, 6b adapted to rotate the reflecting mirror 32 or the beam splitter 34.

These levers 6a, 6b are each composed of a head part 61 and a shank 63 smaller in diameter than the head part 61. On the head parts 61, linear indexes 62 are formed one each.

Further, on the proximal end side of the sheath 2, the long hole (guiding groove) 24 for guiding the levers 6a, 6b is formed. This long hole 24 is formed parallel to the longitudinal axis of the sheath 2 and is adapted to communicate with the working lumen 21. The width of this long hole 24 (the length in the vertical direction in the bearings of the diagram) is larger than the outside diameter of an axial parts 63 of the levers 6a, 6b and smaller than the head part 61.

The shanks 63 of the levers 6a, 6b are respectively inserted in the long hole and the head parts 6a of the levers 6a, 6b are positioned on the outer peripheral side of the sheath 2 as illustrated in FIG. 19A. The graduated scale 25 is disposed along the longitudinal axis of the sheath 2 near the long hole 24 (on the lower side of the long hole 24 in the bearings of the diagram) on the outer peripheral surface of the sheath 2. This graduated scale 25 corresponds to the angles θ3 and θ4, namely to the target position 5.

By reading the value of the graduated scale 25 which coincides with the index 62 of the lever 6a and the value of the graduated scale 25 which coincides with the index 62 of the lever 6b, therefore, the target position 5 can be comprehended and particularly the distance between the target position 5 and the outer peripheral surface of the sheath 2 (the surface of the tissue) in the direction perpendicular to the longitudinal axis of the sheath 2, namely the depth of the target position 5, can be comprehended based on the scale reading.

To be more specific, with the distance M between the shaft 322 supporting the reflecting mirror 32 and the shaft 342 supporting the beam splitter 34 set at 20 mm, for example, the graduated scale 25 has the center thereof marked as "0" and has both sides thereof across the "0" calibrated each into 30 equal parts. In this case, the scale is so set that one part of the calibration may correspond to the angle to be formed between the line perpendicular to the optical axis of the shaft 322 or 342 of the reflecting mirror 32 or beam splitter 34 and the reflected ray (the angle indicated as −α or +α in FIG. 18).

Owing to this arrangement, the value of the graduated scale 25 which is pointed by the index 62 of the lever 6a represents the angle of the reflected light of the reflecting mirror 32 or beam splitter 34. By reading the values of the graduated scale 25 which are pointed by the indexes 62 of the levers 6a, 6b, therefore, the target position 5 (the distance L2 to the position of the center of irradiation) can be comprehended based on the scale readings.

It is assumed that "D1" stands for the outside diameter of the sheath 2, "L2" for the distance from the shaft 322 to the position of center of irradiation, and "D2" for the depth of irradiation from the shafts 322, 342 to the position of center of irradiation as illustrated in FIG. 18. Then "L2" and "D2" mentioned above relative to the readings of the levers 6a, 6b relative to the graduated scale 25 have such values as are indicated in the table of FIG. 19B. For example, the position of irradiation, L2, is 13.5 mm and the depth of irradiation, D2, is 37.0 mm when the outside diameter, D1, of the sheath is 7 mm, the reading of the lever 6a on the graduated scale 25 is −10, and the reading of the lever 6b on the graduated scale 25 is +20.

In FIG. 19B, some of the numerical values are missing from the table because such numerical values are not necessary where the beams of light reflected by the reflecting mirror 32 and the beam splitter 34 either intersect at a very remote point or fail to intersect at all.

Now, the operation of this laser irradiating device 1 will be described below.

When the operator grips the head part 61 of the lever 6a, i.e. the means for altering the direction of emission, and moves the lever 6a, the lever 6a slides along the long hole 24 and, at the same time, the guide member 321 moves in the longitudinal direction of the sheath 2, with the result that the reflecting mirror 32 rotates to a prescribed direction. Thus, the angle θ3 is altered.

When the operator grips the head part 61 of the lever 6b and moved this lever 6b, the lever 6b slides along the long hole 24 and, at the same time, the guide member 341 moves in the longitudinal direction of the sheath 2, with the result that the beam splitter 34 rotates to a prescribed direction. Thus, the angle θ4 is altered.

Though this laser irradiating device 1 brings the same effect at the laser irradiating device 1 of the preceding embodiment, particularly this Embodiment 8 produces the effect of facilitating the alteration of the direction of emission of the laser beams by the motion of the guide members 321, 341, namely the rotation of the reflecting mirror 32 and the beam splitter 34 because this device is provided with the levers 6a, 6b.

Since the target position 5 (particularly the depth of the target position 5) can be comprehended by reading the value of the graduated scale 25 which coincides with the index 62 of the lever 6a and the value of the graduated scale 25 which coincides with the index 61 of the lever 6b, the target position 5 can be easily and infallibly moved to a position aimed at (particularly the depth of the target position 5 can be altered to a depth aimed at). As a result, the target part 120 for irradiation can be easily and infallibly heated uniformly to a necessary temperature while retaining the site other than the target part 120 for irradiation at a relatively low temperature.

<<Embodiment 9>>

Figure 20:
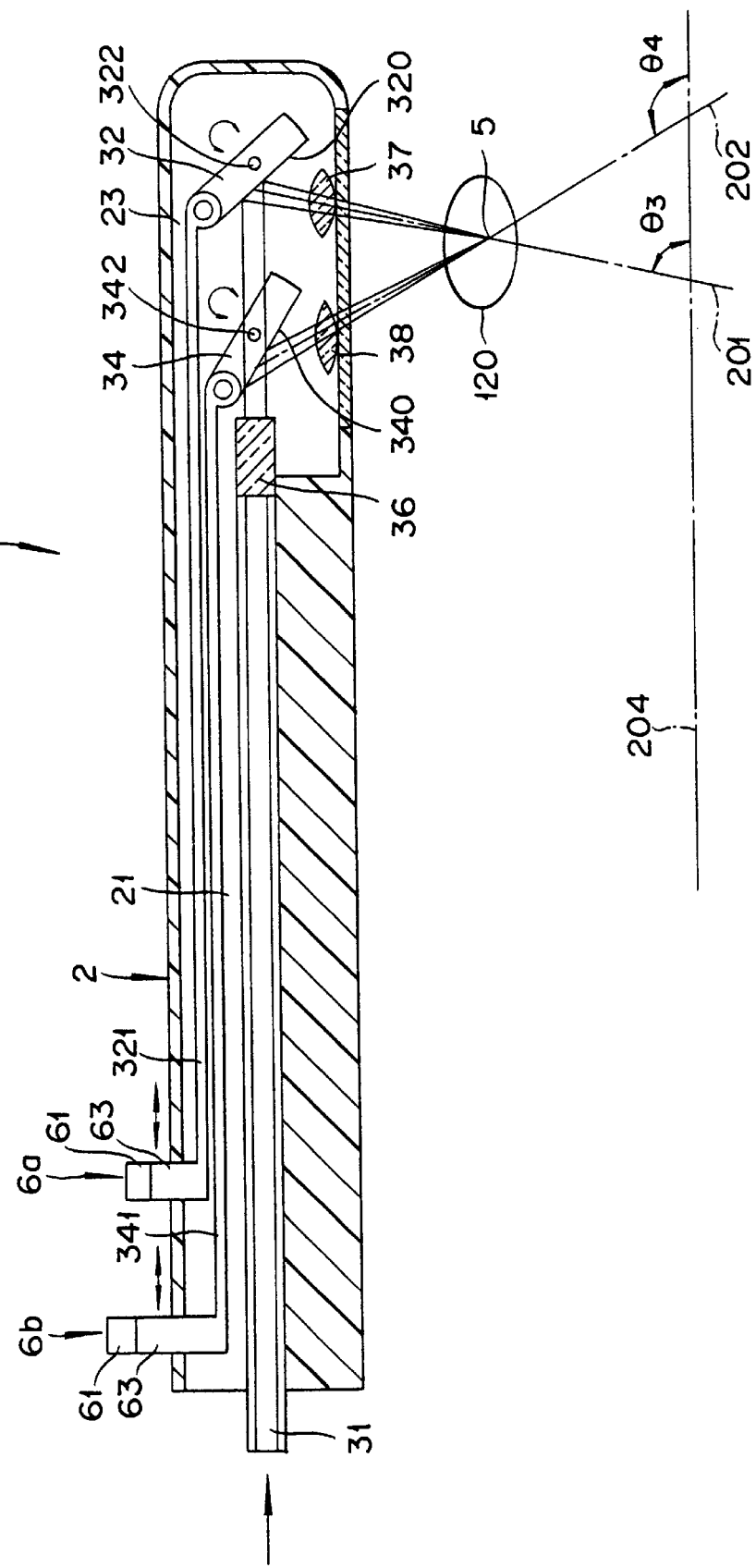
FIG. 20 is a cross section illustrating a necessary portion of a laser irradiation device according to Embodiment 9 of this invention.

FIG. 20 is a cross section illustrating the Embodiment 9 of the laser irradiating device of this invention. The component parts which are shared by this Embodiment 9 and the embodiments cited above will be omitted from the following description. The main points of difference between the two embodiments in question will be described below.

As illustrated in the diagram, the laser irradiating device 1 is provided on the laser beam emitting side of the reflecting mirror 32 (the lower side in the bearings of the diagram) with the converging lens (condensing lens) 37.

Further, it is provided on the laser beam emitting side of the beam splitter 34 (the lower side in the bearings of the diagram) with a converging lens (condensing lens) 38.

Now, the operation of this laser irradiating device 1 will be described below.

The laser beam which has been injected into the optical fiber 31 via the proximal end part thereof is guided by the optical fiber 31 from the proximal end part through the distal end part and transformed by the collimating lens 36 into a collimated ray. Part of the collimated ray is reflected by the splitting face 340 of the beam splitter 34 and the remainder thereof is passed through the splitting face 340 (the collimated ray split into a reflected ray and a transmitted ray). The laser beam which has been reflected by the splitting face 340 of the beam splitter 34 is transformed by the converging lens 38 into a convergent ray and made to impinge on the target position 5.

The laser beam (collimated ray) which has passed the splitting face 340 of the beam splitter 34 is reflected by the reflecting face 320 of the reflecting mirror 32. The reflected ray is transformed by the converging lens 37 into a convergent ray and made to impinge on the target position 5.

That is to say, the laser beam guided by the optical fiber 31 is transformed by the collimating lens 36 into a collimated ray and then split into two parts by the beam splitter 34. The split laser beams (the laser beam reflected by the reflecting face of the reflecting mirror 32 and the laser beam reflected by the splitting face 340 of the beam splitter 34) are respectively transformed into convergent rays and passed through different routes and converged on the target position 5.

Though this Embodiment 9 brings the same effect as the preceding embodiment, particularly the present Embodiment 9 uses a convergent ray for irradiation and therefore produces the effect of enhancing the concentration of the laser beam at the target position 5 and exalting the energy densities of the laser beams at the target position and in the neighborhood thereof as compared with the case of using a diffuse ray for irradiation. In other words, the present embodiment can prevent the surface layer part from injury with enhanced infallibility because it can lower the energy densities of the laser beams which impinge on the surface layer part as compared with the case of using a disperse ray for irradiation, providing that the energy densities of the laser beams which impinge on the target position are fixed.

Figure 21:
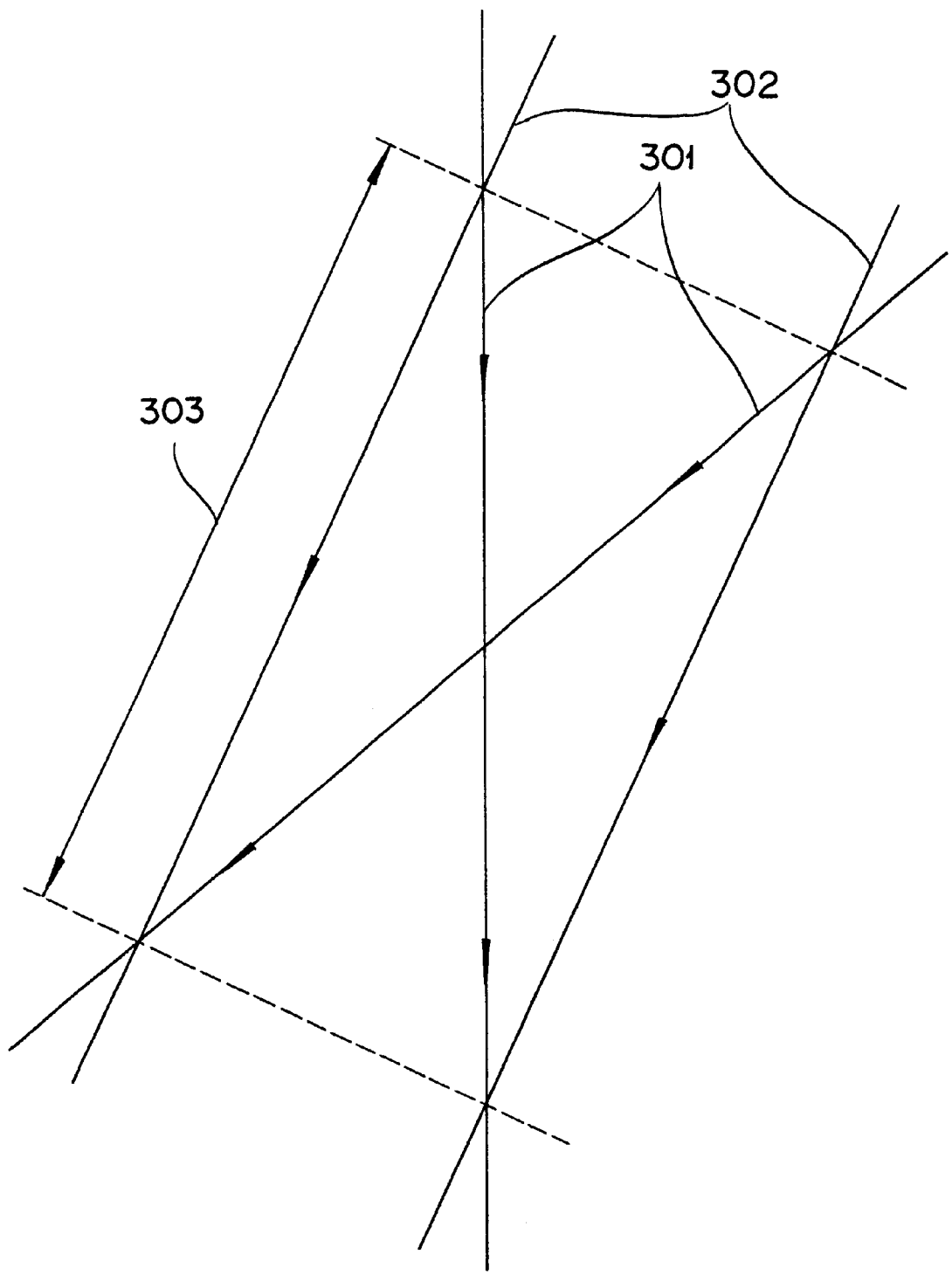
FIG. 21 is a diagram illustrating a converging beam and a parallel beam.

FIG. 21 is a diagram illustrating the irradiated laser beam (convergent ray) of the present embodiment and the irradiated laser beam (collimated ray) of the present embodiment as type specimens. As illustrated in this diagram, since the laser beam 301 which is a convergent ray is once converged and then diverged, it is at an advantage in forming a small beam diameter in the range 303 and heightening the energy densities of the laser beams as compared with the laser beam 302 which is a collimated ray.

<<Embodiment 10>>

Figure 22:
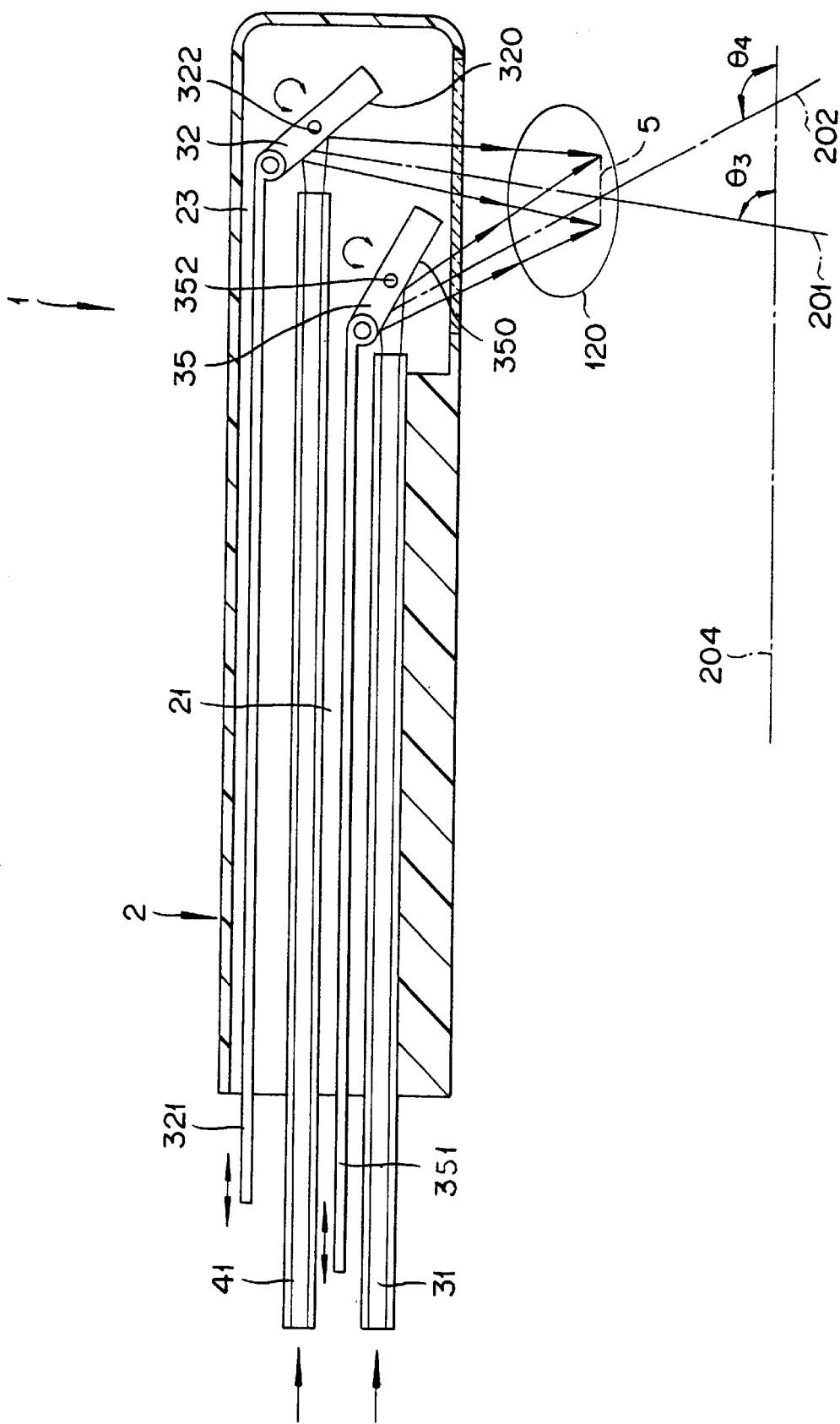
FIG. 22 is a cross section illustrating a necessary portion of a laser irradiation device according to Embodiment 10 of this invention.

FIG. 22 is a cross section illustrating a necessary portion of the Embodiment 10 of the laser irradiating device of this invention. The component parts which are shared by this Embodiment 10 and the embodiments cited above will be omitted from the following description. The main points of difference between the two embodiments in question will be described below.

As illustrated in this diagram, the laser irradiating device 1 has installed within the working lumen 21 of the sheath 2 the optical fibers (light guiding members) 31, 41, the reflecting mirrors (emitting parts) 32, 35, and the rodlike guide members 321, 351.

The optical fiber 41 is positioned on the upper side of the optical fiber 31 in the bearings of the diagram and the distal end part thereof is positioned on the forward end side from the distal end part of the optical fiber 31 (the right side in the bearings of the diagram).

The reflecting mirror 35 is positioned on the distal end side (distal end part 23) of the optical fiber 31 and is supported by the shaft 352 rotatably relative to the sheath 2. Further, the reflecting mirror 35 at the end part thereof is supported rotatably by the distal end part of the guide member 351.

The reflecting mirror 32 is positioned on the distal end side (the distal end part 23) of the optical fiber 41 and is supported by the shaft 322 rotatably relative to the sheath 2. Further, the reflecting mirror 32 at the terminal part thereof is supported rotatably by the distal end part of the guide member 321. The shaft 322 supporting the reflecting mirror 32 and the shaft 352 supporting the reflecting mirror 35 are disposed parallel to each other.

Now, the operation of this laser irradiating device 1 will be described below.

The laser beam which has entered the optical fiber 31 via the proximal end part thereof is guided by the optical fiber 31 from the proximal end part through the distal end part and reflected by the reflecting face 350 of the reflecting mirror 35. The reflected ray is made to impinge on the target position 5.

The laser beam which has entered the optical fiber 41 via the proximal end part thereof is guided by the optical fiber 41 from the proximal end part through the distal end part and reflected by the reflecting face 320 of the reflecting mirror 32. The reflected laser beam is made to impinge on the target position 5.

That is to say, the laser beam reflected by the reflecting mirror 32 and the laser beam reflected by the reflecting mirror 35 are passed through different routes and then converged on the target position 5.

The present embodiment brings the same effect as the embodiments described above.

<<Embodiment 11>>

Figure 23:
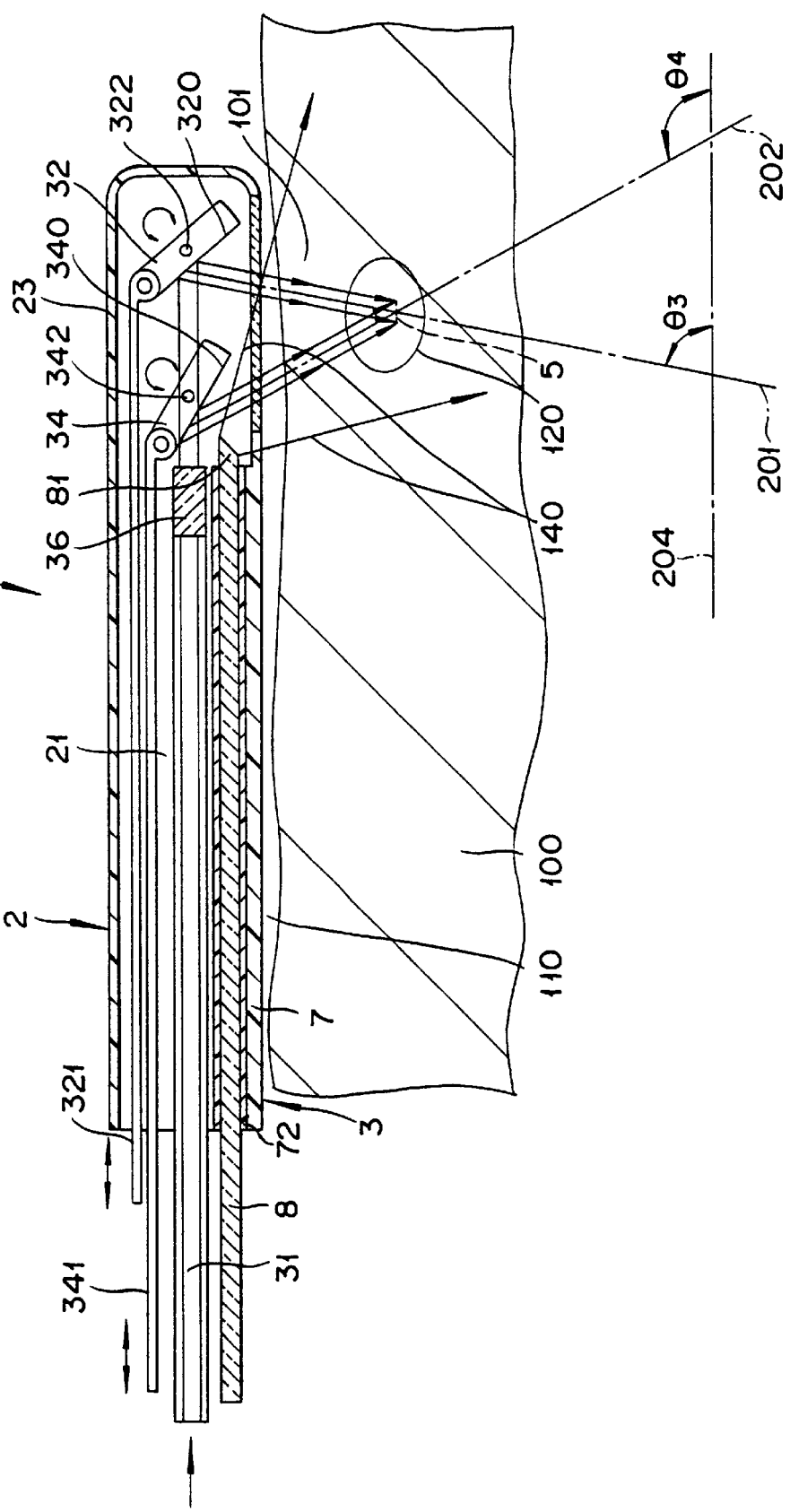
FIG. 23 is a cross section illustrating a necessary portion of a laser irradiation device according to Embodiment 11 of this invention.

FIG. 23 is a cross section illustrating a necessary portion of the Embodiment 11 of the laser irradiating device of this invention. The component parts which are shared by this Embodiment 11 and the embodiments cited above will be omitted from the following description. The main points of difference between the two embodiments in question will be described below.

The laser irradiating device 1 illustrated in the diagram has formed in the sheath 7 of the laser probe 3 an endoscope grade lumen 72 adapted for permitting removal insertion therein of an endoscope 8.

This lumen 72 is formed on the lower side of the optical fiber 31 in the bearings of the diagrams (on the laser beam emitting side) parallel to the longitudinal axis of the sheath 7, opened in the proximal end of the sheath 2, and adapted to communicate with the working lumen 71.

This laser irradiating device 1 is prepared for use, for example, by inserting the endoscope 8 for oblique inspection (for the inspection of the oblique front) or the endoscope for wide-angle front inspection into the lumen 72 and locating a distal end part 81 of the endoscope 8 in the distal end part of the sheath 2, namely in the proximity of the beam splitter 34.

By this endoscope 8, the operator is enabled to inspect the state of things arising within a range of observation 140 to be seen via a light path such as, for example, the position for irradiation of the laser beam, the direction of irradiation of the laser beam (the direction of emission of the laser beam), and the condition of the surface of the tissue 100 irradiated by the laser beam.

The range of observation 140 mentioned above is enabled to assume an arbitrary position by rotating the endoscope 8 round the longitudinal axis thereof or moving it in the longitudinal direction thereof.

Though the present Embodiment 11 brings the same effect as the embodiments cited above, particularly this Embodiment 11 relies on the endoscope 8 to attain necessary inspection of the range of observation 140 and consequently produces the effect of visually confirming the relative position of the target part 120 on the surface of the tissue 100, the position to be irradiated with the laser beam, and the direction of irradiation. As a result, the operator is enabled to irradiate the target part 120 more reliability with the laser beam and, during the irradiation of the laser beam, observe the conditions of the surface of the tissue 100 irradiated with the laser beam, and optimize the conditions of irradiation based on the result of the observation. While the present Embodiment 11, as depicted above, causes the endoscope 8 to be inserted removably into the lumen 72, this invention alternatively allows the endoscope 8 to be installed in a fixed state to the sheath 7. The present invention, however, does not impose any particular restriction on the construction of the endoscope 8 to be used therein.

<<Embodiment 12>>

Figure 24:
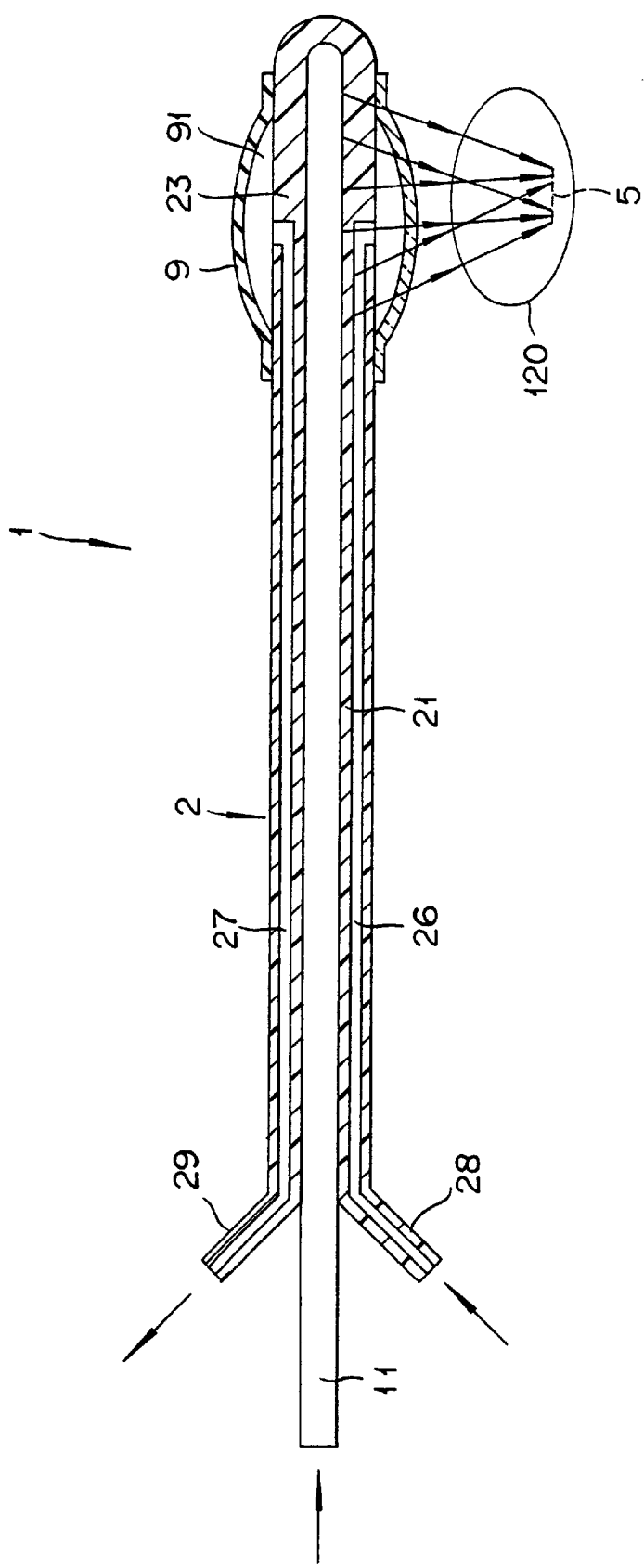
FIG. 24 is a cross section a necessary portion of illustrating by way of specimen part of a laser irradiation device according Embodiment 12 of this invention.

FIG. 24 is a cross section illustrating a necessary portion of the Embodiment 12 of the laser irradiating device of this invention partly by way of a type specimen. The component parts which are shared by this Embodiment 12 and the embodiments cited above will be omitted from the following description. The main points of difference between the two embodiments in question will be described below.

The laser irradiating device 1 illustrated in the diagram is provided at the distal end part 23 of the sheath 2 with a balloon 9 adapted to allow inflation and contraction. The part at least in the lower side of this balloon 9 in the bearings of the diagram is pervious to light.

The material for forming this balloon 9 is preferred to excel in perviousness to the laser beam. As concrete embodiments of the material answering this description, polyolefins, polyesters, polyamides, latexes, and cellulose may be cited. This choice of the material can alleviate such phenomena as loss of energy and evolution of heat which occur in the balloon 9 in consequence of the absorption of the laser beam.

In the sheath 2, an inflation lumen (flow path) 26 for supplying a working fluid for inflating the balloon 9 and a deflation lumen (flow path) 27 for discharging the working fluid mentioned above are respectively formed.

These lumens 26, 27 are opened respectively into a supply part 28 and a discharge part 29 formed on the proximal end side of the sheath 2 for handling the working fluid and adapted to communicate with a hollow part 91 of the balloon 9 at the distal end part 23 of the sheath 2.

These lumens 26, 27 are disposed as symmetrized across the longitudinal axis of the sheath 2. The working lumen 21 of the sheath 2 is opened on the proximal end side thereof.

In this working lumen 21, the aggregate 11 which comprises the laser probe 3 illustrated in FIG. 17 cited above, the reflecting mirror 32, the guide member 321 supporting the reflecting mirror 32, the beam splitter 35, and the guide member 351 for supporting this beam splitter 35 is installed. These component parts are independently installed movably in the longitudinal direction of the sheath 2.

The working fluid mentioned above does not need to submit to any particular restriction but requires only to be capable of inflating and contracting the balloon 9. It is nevertheless preferred to be a refrigerant. For, the refrigerant prevents the surface layer part of the tissue more reliably from sustaining an injury by cooling the surface layer part during the course of the laser irradiation.

When the target part 120 happens to be the prostate gland, for example, the irradiation of the laser beam is preferred to be implemented in such a manner that the temperature of the target part 120 may fall in the approximate range of 48–100° C. and the temperatures of the site of the upper side and the site of the lower side of the target part 120 in the bearings of the diagram may respectively remain below 44° C. The laser irradiating device 1 of this embodiment is capable of effecting the laser beam irradiation according to this plan.

The temperature of the refrigerant mentioned above does not need to submit to any particular restriction but requires only to be capable of cooling the surface layer part of the tissue. The proper temperature of the refrigerant does not exceed 37° C., preferably falls in the approximate range of 0–25° C., and more preferably falls in the approximate range of 0–10° C.

The working fluid to be used in this case is preferred to be physiological saline solution. The use of the physiological saline solution is at an advantage in allaying the effect of leakage thereof which possibly occurs intracorporeally by some cause or other.

When the refrigerant is adopted as the working fluid, the refrigerant is preferred to be circulated. Advantageously, this circulation of the refrigerant is continued from before the laser irradiation till after the laser irradiation is completed.

The efficiency of the cooling can be improved by circulating the refrigerant. The surface layer part can be cooled to an increased extent by continuing the circulation of the refrigerant from before the laser irradiation till after the laser irradiation is completed.

The discharge part 29 is preferred to be provided, for example, with a pressure valve which opens when the internal pressure thereof surpasses a prescribed level. As a result, the balloon 9 can be inflated with a prescribed pressure without relying on the flow volume of the refrigerant.

The temperature of the refrigerant and the flow volume of the refrigerant are preferred to be controlled as synchronized with the irradiation of the laser. As a result, the surface layer part can be prevented from being cooled or heated excessively.

Further, the balloon 9 is preferred to be provided with a temperature sensor for detecting the surface temperature of the tissue. In this case, the temperature sensor serves the purpose of detecting the surface temperature of the tissue and allowing the information (value of detection) consequently obtained to be utilized in controlling the cooling operation. As a result, the cooling can be efficiently implemented to a necessary and sufficient extent.

Now, the operation of the Embodiment 12 will be described below.

The laser irradiating device 1, with the balloon 9 in a contracted state, is inserted as led by the distal end part 23 into the body cavity until the distal end part 23 thereof settles on the upper side of the target place 120 in the bearings of the diagram.

When the refrigerant (working fluid) emanating from the supply part 28 is injected by means of a pump connected to the supply part 28, this refrigerant flows from the supply part 28 via the inflation lumen 26 into the hollow part 91 formed in the balloon 9, with the result that the balloon 9 will be inflated to a prescribed size.

The inflation of the balloon 9 results in fixing the position and direction of the part to be irradiated with the laser beam. Consequently, the target part 120 can be irradiated easily and infallibly with the laser beam.

By inflating the balloon 9 thereby pressing the tissue in the direction from the surface toward the deep part under a prescribed pressure, the tissue is compressed into a bloodless state or the light path for the laser beam from the laser irradiating device 1 through the target part 120 is reduced in length. As a result, the laser beam is passed with added ease and the therapeutic effect is heightened.

The consequence is that the part contacting the balloon 9 and the neighborhood thereof, namely the surface layer part of the tissue, is cooled with the refrigerant. As a result, the rise of temperature due to the laser irradiation can be precluded and the surface layer part can be infallibly prevented from sustaining an injury.

The circulation of the refrigerant is implemented by injecting the refrigerant from the supply part 28 and discharging it via the discharge part 29. In this case, the refrigerant emanates from the supply part 28, passes via the inflation lumen 26, and flows into the hollow part 91 formed in the balloon 9. The refrigerant which has flowed into the hollow part 91 flows at least semicircularly (circulates) inside the hollow part 91 and then passed through the deflation lumen 27 and finally discharged from the discharge part 29.

During the extraction of the laser irradiating device 1 from the body cavity after completion of the irradiation of the target part 120 with the laser beam, the discharge of the refrigerant from the discharge part 29 alone is performed without continuing the injection of the refrigerant from the supply part 28. Then, the balloon 9 is contracted by discharging the refrigerant in the hollow part 91 of the balloon 9 via the deflation lumen 27.

The laser irradiating device 1, with the balloon 9 in a contracted state, is wholly moved to the left side in the bearings of the diagram and extracted from within the body cavity.

Though this Embodiment 12 brings the same effect as the embodiments cited above, particularly the present Embodiment 12 uses the balloon 9 in the manner described above and consequently produces the effect of easily and infallibly fixing the position and the direction of the part to be irradiated with the laser beam.

Further, the present embodiment is capable of cooling the surface layer part of the tissue with the refrigerant held in the balloon 9 and consequently precluding the rise of temperature due to the laser irradiation.

The present invention allows the preceding embodiment to have the balloon 9 provided in the sheath 2 in the same manner as in the present embodiment.

<<Embodiment 13>>

Figure 25:
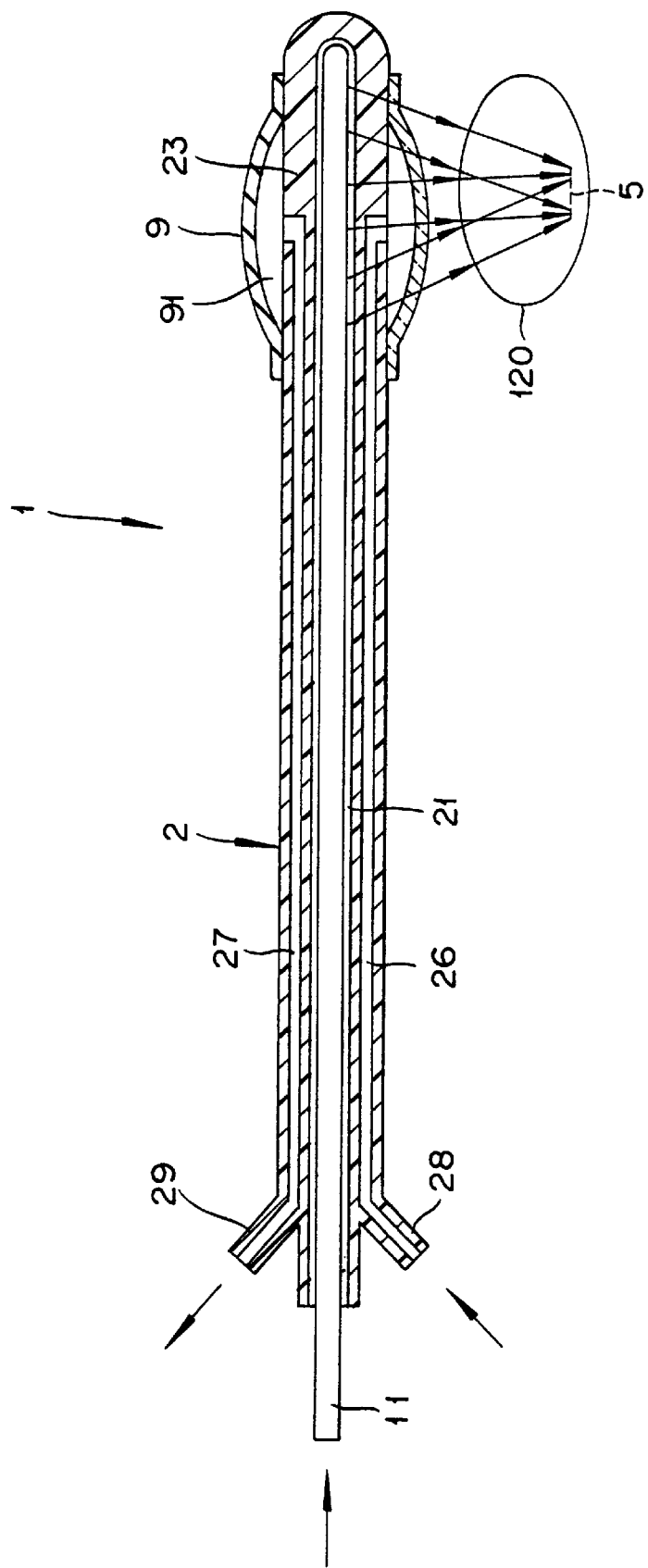
FIG. 25 is a cross section a necessary portion of illustrating by way of specimen part of a laser irradiation device according to Embodiment 13 of this invention.

FIG. 25 is a cross section illustrating a necessary portion of the Embodiment 13 of the laser irradiating device of this invention partly by way of a type specimen. The component parts which are shared by this Embodiment 13 and the Embodiment 12 cited above will be omitted from the following description. The main points of difference between the two embodiments in question will be described below.

The laser irradiating device 1 illustrated in the diagram has inserted removably in the working lumen 21 of the sheath 2 the aggregate 11, specifically the aggregate 11 which, as illustrated in FIG. 17, comprises the laser probe 3, the reflecting mirror 32, the guide member 321 supporting the reflecting mirror 32, the beam splitter 34, and the guide member 341 supporting the beam splitter 34.

Though this Embodiment 13 brings the same effect as the embodiments cited above, particularly the present Embodiment 13 uses the aggregate 11 which is inserted removably in the working lumen 21 of the sheath 2 and therefore produces the effect of adapting the sheath 2 contacting the tissue as a disposable component and allowing the aggregate 11 held therein to be exchanged after use. Especially, this embodiment affords the advantage of alleviating the burden on the patient because the aggregate 11 can be exchanged for a new supply while the sheath 2 is kept inserted in the body cavity.

<<Embodiment 14 >>

This Embodiment 14 is not illustrated in the accompanying drawings. The component parts which are shared by this embodiment and the Embodiments 12, 13 cited above will be omitted from the following description. The main points of difference between the two embodiments in question will be described below.

This Embodiment 14 has a surface layer containing a hydrophilic macromolecular material formed on the surface of the sheath 2 or on the surfaces of the sheath 2 and the balloon 9.

As concrete embodiments of the hydrophilic macromolecular material which proves favorable herein, carboxymethyl cellulose, polysaccharides, polyvinyl alcohol, polyethylene oxide, sodium polyacrylate, methyl vinyl ether-maleic anhydride copolymer, and water-soluble polyamides may be cited. Among other hydrophilic macromolecular materials mentioned above, methyl vinyl ether-maleic anhydride copolymer proves particularly advantageous.

When the surface layer of the laser irradiating device 1 of this construction is immersed such as in physiological saline solution prior to the use of the device, the surface layer is wetted and consequently enabled to impart lubricity to the surface of the laser irradiating device 1.

Though this Embodiment 14 brings the same effect as the preceding embodiments, particularly the present Embodiment 14 contains the surface layer including the hydrophilic macromolecular material and therefore produces the effect of diminishing the friction of the laser irradiating device 1 against the tissue and consequently alleviating the burden on the patient and, at the same time, enhancing the safety of the device for the patent.

To be specific, this embodiment permits the insertion of the laser irradiating device 1 into the body cavity, the extraction thereof from within the body cavity, and the movement and rotation thereof inside the body cavity to be carried out smoothly.

The laser irradiating device of this invention is a device for medical care and is used for the cure of prostatomegaly and various ulcers (such as, for example, cancers).

While the laser irradiating device of this invention has been described with particular reference to specific embodiments illustrated in the accompanying drawings, it is evident that this invention does not need to be limited thereto. The components thereof may be substituted by those of arbitrary construction which fulfill the same functions.

For example, this invention may be embodied by suitably combining the characteristics of the embodiments cited above.

Further, in the present invention, the light conducting member does not need to be limited to the optical fiber. Optionally, a rod lens, for example, may be used instead.

Then, in the present invention, the emitting part does not need to be limited to those depicted in the embodiments cited above. Optionally, a prism or a wedge plate may be adopted instead.

The entire disclosure of Japanese Patent Applications Nos. 10-103908 and 10-103909 filed on Mar. 31, 1998, including the specification, claims, drawings and summary are incorporated herein by reference in their entirety.

What is claimed is:

1. A lateral-irradiation type laser irradiating device for irradiating a tissue with laser beams capable of reaching a depth in the organism, comprising
an elongate main body,
at least one light guiding member disposed in said main body and adapted to guide said laser beams,
emitting means provided with a plurality of emitting parts for laterally or obliquely issuing said laser beams guided by said light guiding member so that said laser beams pass through different routes and converge towards one another at a target position in the organism to treat the tissue, and
an emitting direction altering means for altering the direction of emission of the laser beam emitting from at least one of said emitting parts,
whereby said target position is moved by altering the direction of emission of said laser beams by the use of said emitting direction altering means.

2. A laser irradiating device according to claim 1, which further comprises a splitting means for splitting said laser beams guided by said light guiding member into a plurality of laser beams.

3. A laser irradiating device according to claim 1 or claim 2, wherein said emitting direction altering means is adapted to move said target position in at least one direction selected from among the direction perpendicular to the longitudinal axis of said main body, the longitudinal direction along the longitudinal axis of said main body, and the circumferential direction round the longitudinal axis of said main body.

4. A laser irradiating device according to claim 3, wherein said emitting direction altering means is adapted to effect said motion of said target position by moving at least one of said emitting parts in the direction of the longitudinal axis of said main body.

5. A laser irradiating device according to claim 4, wherein said emitting parts are so disposed that the light guiding members may be vertically superposed and the emitting part disposed in the lower light guiding member emits the laser beam in the direction oblique to the distal end side and the emitting part disposed in the upper light guiding member emits the laser beam in the direction oblique to the proximal end side.

6. A laser irradiating device according to claim 3, wherein said emitting direction altering means is adapted to effect said motion of said target position by altering the angle with which said emitting part is inclined relative to the longitudinal axis of said main body.

7. A laser irradiating device according to claim 3, wherein said emitting direction altering means is adapted to effect the motion of said target position in the circumferential direction round the longitudinal axis of said main body by rotating at least said emitting part round the longitudinal axis of said main body.

8. A laser irradiating device according to claim 2, wherein said splitting means is an optical element wherein at least one of said emitting parts reflects part of said laser beams and passing the remainder thereof.

9. A laser irradiating device according to claim 8, which is constructed so that the laser beams from the emitting parts are substantially equal in quantity of light.

10. A laser irradiating device according to claim 1, wherein said emitting member is provided with a reflecting face for reflecting at least part of the laser beam injected into said emitting part.

11. A laser irradiating device according to claim 1, wherein said emitting direction altering means is provided with a moving means for altering the interval between said emitting members by moving at least one of said emitting parts in the direction of the longitudinal axis of said main body.

12. A laser irradiating device according to claim 11, wherein said moving means is provided with an operating member capable of producing an operation of motion.

13. A laser irradiating device according to claim 10, wherein said moving means is provided with a graduated scale corresponding to the intervals between said emitting parts or the positions of said emitting parts.

14. A laser irradiating device according to claim 1, wherein said emitting means is disposed in the distal end part of said light guiding member.

15. A laser irradiating device according to claim 1, which further comprises an optical system adapted to transform said laser beam into a collimated ray or a convergent ray and disposed halfway in the lengths of light paths for the laser beams.

16. A laser irradiating device according to claim 1, wherein said main body is provided with a lumen allowing insertion therein of an endoscope.

17. A laser irradiating device according to claim 1, which further comprises a balloon capable of inflation and contraction disposed in the distal end part.

18. A laser irradiating device according to claim 1, wherein said main body is provided on the surface thereof with a surface layer containing a hydrophilic macromolecular material.

19. A laser irradiating device according to claim 1, wherein said laser beams have a wavelength in the approximate range of 700–1300 nm.

20. A method for the therapy of prostate gland comprising guiding laser beams capable of reaching a depth in the organism along at least one light guiding member toward respective emitting parts, laterally emitting said laser beams via different routes from the respective emitting parts so that the laser beams converge towards one another at a target position in the organism, adjusting at least one of the emitting parts to alter the direction of emission of the laser beam emitted from the at least one emitting part and thereby move the target position, and irradiating an ailing site of prostate gland with the laser beams.

21. A method according to claim 20, wherein said laser beams are irradiated in such a manner that the temperature of the ailing site of said prostate gland reaches a level in the approximate range of 48–100° C. and the temperature above or below said ailing side remains below 44° C.

22. A method according to claim 20, wherein said main body is provided in the distal end part thereof with a balloon adapted to inflate or contract and allow passage of a working fluid in the interior thereof and said working fluid is enabled to cool the surface layer part of the tissue preferably to a temperature not exceeding 37° C., more preferably to a temperature falling in the range of 0–25° C., and still more preferably to a temperature in the range of 0–10° C.

* * * * *

UNITED STATES PATENT AND TRADEMARK OFFICE
CERTIFICATE OF CORRECTION

| | |
|---|---|
| PATENT NO. | : 6,520,959 B1 |
| DATED | : February 18, 2003 |
| INVENTOR(S) | : Shigenobu Iwahashi et al. |

It is certified that error appears in the above-identified patent and that said Letters Patent is hereby corrected as shown below:

Column 31,
Line 8, change "10" to -- 12 -- so that Claim 13 properly depends from Claim 12 rather than Claim 10.

Signed and Sealed this

Eighth Day of November, 2005

JON W. DUDAS
*Director of the United States Patent and Trademark Office*